US010974041B2

(12) United States Patent
Chew et al.

(10) Patent No.: US 10,974,041 B2
(45) Date of Patent: Apr. 13, 2021

(54) NEUROMODULATION DEVICE

(71) Applicants: GALVANI BIOELECTRONICS LIMITED, Brentford (GB); ACADEMISCH MEDISCH CENTRUM, Amsterdam (NL)

(72) Inventors: Daniel John Chew, Stevenage (GB); Wouter Jacob De Jonge, Amsterdam (NL); Hans Jakob Kristoffer Famm, Stevenage (GB); Sonal Patel, Basel (CH); Olaf Welting, Amsterdam (NL)

(73) Assignees: GALVANI BIOELECTRONICS LIMITED, Middlesex (GB); ACADEMISCH MEDISCH CENTRUM, Amsterdam (NL)

( * ) Notice: Subject to any disclaimer, the term of this patent is extended or adjusted under 35 U.S.C. 154(b) by 137 days.

(21) Appl. No.: 15/568,964

(22) PCT Filed: Apr. 22, 2016

(86) PCT No.: PCT/IB2016/052307
§ 371 (c)(1),
(2) Date: Oct. 24, 2017

(87) PCT Pub. No.: WO2016/170510
PCT Pub. Date: Oct. 27, 2016

(65) Prior Publication Data
US 2018/0117319 A1 May 3, 2018

Related U.S. Application Data

(60) Provisional application No. 62/152,119, filed on Apr. 24, 2015.

(51) Int. Cl.
*A61N 1/36* (2006.01)
*A61N 1/05* (2006.01)

(52) U.S. Cl.
CPC ......... *A61N 1/0551* (2013.01); *A61N 1/0556* (2013.01); *A61N 1/3605* (2013.01); *A61N 1/36007* (2013.01); *A61N 1/36135* (2013.01)

(58) Field of Classification Search
CPC ............... A61N 1/3605; A61N 1/3606; A61N 1/36085; A61N 1/0509; A61N 1/0507; A61N 1/0551
See application file for complete search history.

(56) References Cited

U.S. PATENT DOCUMENTS

2005/0075701 A1* 4/2005 Shafer ............... A61N 1/36017
607/72
2005/0075702 A1 4/2005 Shafer
(Continued)

FOREIGN PATENT DOCUMENTS

JP 2008-525102 A 7/2008
JP 2015-502820 A 1/2015
(Continued)

OTHER PUBLICATIONS

International Search Report dated Sep. 20, 2016 issued in PCT/IB2016/052307.
(Continued)

*Primary Examiner* — Alyssa M Alter
(74) *Attorney, Agent, or Firm* — Scully, Scott, Murphy & Presser, P.C.

(57) ABSTRACT

The invention provides devices, apparatuses, systems and methods for treating and ameliorating inflammation of the gut. In particular, the invention provides devices, apparatuses and methods in which a neuromodulatory signal is delivered a splenic nerve and/or superior mesenteric plexus (SMP). The signal is able to treat inflammatory disorders, e.g., colitis, for example in Inflammatory Bowel Disease.

15 Claims, 17 Drawing Sheets

(56) References Cited

U.S. PATENT DOCUMENTS

| | | | |
|---|---|---|---|
| 2006/0116736 A1 | 6/2006 | DiLorenzo | |
| 2009/0275997 A1* | 11/2009 | Faltys | A61N 1/0553 607/2 |
| 2013/0178910 A1* | 7/2013 | Azamian | A61B 18/06 607/33 |

FOREIGN PATENT DOCUMENTS

| | | |
|---|---|---|
| WO | 2006/073484 A2 | 7/2006 |
| WO | 2013/086461 A1 | 6/2013 |
| WO | 2013/134541 A2 | 9/2013 |
| WO | WO 2014/153223 A1 | 9/2014 |

OTHER PUBLICATIONS

Office Action dated Apr. 24, 2020 received in European Patent Application No. EP 16 721 943.5.

\* cited by examiner

A

B

A

B

A

B

A

B

C

D

E

F  G

Spontaneous Colitis in sympathectomized RAG mice (Goblet cell depletion)

NEUROMODULATION DEVICE

CROSS-REFERENCE TO RELATED APPLICATIONS

This application claims the benefit of U.S. Provisional Application No. 62/152,119 filed on Apr. 24, 2015, the entire contents of which is incorporated herein by reference.

BACKGROUND

Neural mechanisms regulate all key functions of the gastrointestinal tract such as motility, secretion and vaso-regulation. The autonomic nervous system (ANS), acting largely autonomously in that its activities are not under direct conscious control, represents the extrinsic control of the intestine, and is divided in sympathetic and parasympathetic branches. The ANS sympathetic and parasympathetic components originate in the central nervous system (CNS) (with cell bodies in the brainstem and spinal cord); while the enteric nervous system (ENS), resides within the wall of the gastrointestinal tract. The ANS forms the major efferent component of the peripheral nervous system containing integrative neuronal connections and even complete reflex arcs.

Studies in neuroscience and immunology have identified a number of indications for bidirectional interactions between the nervous and immune systems. As with other organs, intestinal immune responses and the development of immunity seem to be influenced by neural reflexes. In the last decade the parasympathetic efferent vagus nerve has been added to this immune-regulation network. This system, designated "the inflammatory reflex", is thought to comprise an afferent (i.e., sensory) arm that senses inflammation, and an efferent arm that inhibits systemic and local immune responses.

Vagal parasympathetic preganglionic fibers originate from motor neurons of the dorsal nucleus of the vagus and synapse with postganglionic parasympathetic neurons within the intestine (e.g., the myenteric plexus). The density of the vagal innervation displays a proximodistal gradient along the intestine with the highest density observed in the duodenum and the lowest density observed in the distal part of the ileum. The large intestine differs from the rest of the gastrointestinal tract in that the vagus nerve provides parasympathetic innervation of the proximal colon but provides little if any neural input to the distal colon.

Vagus (or Vagal) nerve innervation has been shown to have importance in controlling systemic inflammation. In a LPS model of sepsis, vagus nerve stimulation has been shown to exert an anti-inflammatory effect (Borovikova et al. 2000, Nature; 405, 458-462). Relatedly, the spleen and the splenic nerve have also been shown to play an important role in the vagally-mediated inhibition of systemic inflammation (Huston et al. 2006, J. Exp. Med, 203. 1623-1628, incorporated herein by reference). It has further been demonstrated that the systemic anti-inflammatory effect can be induced without vagus nerve signalling if the splenic nerve is stimulated (Vida et al, 2011, J. Immunol. 186: 4340-4346, incorporated herein by reference). However, there has been no demonstration that splenic nerve stimulation can result in any local therapeutic mucosal anti-inflammatory effect.

In more extensive mucosal inflammation (for example Inflammatory Bowel Disease or "IBD"), a potential anti-inflammatory reflex arc of the vagus nerve is observed, but the underlying mechanism is less well established than for systemic inflammation. In general terms, pharmacologic nicotinic agonist activation ameliorates gut inflammation. Similarly, the administration of acetylcholinesterase inhibitors ameliorates experimental colitis via central inhibition. The effect of acetylcholinesterase inhibitors is lost in animals that have undergone a vagotomy, indicating that parasympathetic acetylcholine signalling is involved in vagally mediated anti-inflammatory effects (Pavlov, et al Brain Beh Immun 2009, and Ji et al, Muc Immunol 2014, each of which are incorporated herein by reference).

Intervention in this vagal inflammatory reflex as a form of therapy is currently being investigated in trials of vagus nerve stimulation (VNS). VNS uses implantable devices to stimulate the right carotid vagus in the neck in order to influence levels of inflammation in the gut. However, although VNS is considered to have some positive effects, the mode of action remains to be fully established. Importantly, the vagus nerve is a multifunctional mixed nerve that interacts with many bodily systems, and therefore interventions in vagal signalling are known to have a number of undesirable systemic side-effects, such as cardiac arrhythmia and abnormal respiratory patterns. Accordingly, more specific and targeted methods of neuromodulation for regulating the local mucosal inflammatory response in the spleen and gut (e.g., intestines and colon) are desirable.

SUMMARY OF INVENTION

The present inventors have identified that the innervation of the lower intestine by the vagus nerve is restricted to the proximal colon, with no vagal innervation of the distal colon. This lack of distal innervation may lead to a limited ability to elicit an anti-inflammatory effect in the colon following vagus nerve (vagal) stimulation. However, surprisingly, sympathetic innervation (rather than parasympathetic) of the gut and/or spleen is able to exert an anti-inflammatory effect on the lower intestine (in particular the colon). When such sympathetic innervation is removed, histological and immunological measures of inflammation in the gut increase. The anti-inflammatory effect of sympathetic neural activity is further indicated by the strong inverse correlation between norepinephrine levels in the gut or spleen (indicative of sympathetic activity) and the increased measures of inflammation. The inventors have shown that by stimulating the superior mesenteric plexus (SMP) that includes the Supra Mesenteric Nerve, or the splenic nerve with a neuromodulatory device, it is possible to increase norepinephrine levels in the gut, which will thus reduce the level of colitis-associated inflammation. It has been shown that activation of adrenergic receptors (ARs) results in a reduction in pro-inflammatory cytokine production by dendritic cells (DCs), whether that activation is by adrenergic neurotransmitters (epinephrine) or an artificial AR agonist (salbutamol) (FIG. 1 of Nijhuis. L et al, PLoS One. 2014; 9(1), incorporated herein by reference). Therefore, it would be useful to elicit the increase in tissue NE by neuromodulation of the SMP and/or splenic nerve to produce a local (and optionally systemic) anti-inflammatory effect.

Surprisingly, the inventors have identified that the effect of sympathetic signaling to reduce inflammation does not require the vagus nerve, and therefore is not a downstream result of vagal nerve signaling. Vagotomy had no effect on levels of inflammation (indicating little or no suppressive effect derived from vagal signaling), whereas resection of the sympathetic nerves innervating the gut or the spleen exacerbated the levels of inflammation, indicating that the SMP and splenic nerve are able to suppress inflammation independently of vagal signaling.

Therefore, by modulating the neural activity in these sympathetic nerves (particularly, fibers of the splenic nerve and SMP), the inventors have demonstrated that it is possible to treat (that is, reduce) inflammation associated with colitis. Such a treatment has a particular advantage over stimulation of the vagus nerve in treating inflammation of the colon (i.e., "colitis"), as the large intestine and colon have little parasympathetic vagal innervation, but do have sympathetic innervation. Targeting the splenic nerve and SMP therefore allows new areas of the body to be treated, increasing the specificity and efficacy of neuromodulation. Moreover, by targeting nerves more peripheral than the vagus nerve, the present invention seeks to avoid affecting other bodily systems and thereby reduces unwanted side effects. Thus, the present disclosure provides an apparatus or system for treating an inflammatory disorder in a patient. Favourably, the inflammatory disorder is an inflammatory disorder that includes colitis as a symptom, for example, IBD, such as ulcerative colitis (UC) or Crohn's Disease.

Therefore, in one aspect, the invention provides an apparatus or system for modulating the neural activity of the splenic nerve (or any nerve that innervates the spleen) and/or the SMP of a patient, the apparatus or system comprising: a first transducer configured to apply a first signal to the splenic nerve or SMP and optionally a second transducer to apply a second signal to the other of the SMP or splenic nerve; and a controller coupled to the transducer or transducers, the controller controlling the signal to be applied by the transducer or transducers, such that the signal modulates the neural activity of the nerve to which it is applied to produce a physiological response in the patient. In certain embodiments, the signal applied increases neural activity in the nerve to which the signal is applied.

Preferably, the physiological response elicited is an increase in local sympathetic tone in the spleen and/or gut (e.g., the intestines and/or colon) of the patient. In certain embodiments, the physiological response includes one or more of an increase in gut tissue and/or circulating nor-epinephrine, a decrease in one or more inflammatory markers in gut tissue and/or circulation, a decrease in gut pathology, a decrease in colon fibrosis, and a reduction in one or more symptoms of colitis.

In certain embodiments, the signal is an electrical signal and the transducer is an electrode. In certain such embodiments, the signal is a low frequency AC waveform, optionally having a frequency of 0.01-20 Hz, for example 1.0 Hz.

In certain embodiments, the apparatus or system further comprises a detector element to detect one or more physiological parameters in the patient. In certain such embodiments, the controller is coupled to the detector element, and causes the one or more transducers each to apply the signal when the physiological parameter is detected to be meeting or exceeding a predefined threshold value. In certain embodiments, one or more of the detected physiological parameters is selected from: sympathetic tone; gut tissue and/or circulating nor-epinephrine (NE) levels; gut tissue and/or circulating substance P levels; gut tissue and/or circulating levels of one or more inflammatory markers. In certain embodiments, the one or more detected physiological parameters comprise an action potential or pattern of action potentials in a nerve of the patient.

In another aspect, the invention provides a method of treating colitis in a patient comprising: (i) implanting in the patient a device, an apparatus or a component of a system as described above; (ii) positioning the first transducer of the device, apparatus or system in signalling contact with the splenic nerve and/or SMP of the patient; and (iii) activating the apparatus or system, to modulate neural activity of the splenic nerve (or any nerve that innervates the spleen) and/or SMP.

In certain embodiments, the method is a method of treating IBD, such as treating Crohn's Disease and/or UC.

In another aspect, the invention provides a method of treating colitis in a patient, in particular IBD, the method comprising applying a signal to the splenic nerve (or any nerve that innervates the spleen) and/or the superior mesenteric plexus (SMP) of the patient to modulate the neural activity of the nerve in the patient. In certain embodiments, the signal or signals are applied by a neuromodulation device comprising a transducer configured to apply the signal. In certain such embodiments, the neuromodulation device is at least partially implanted in the patient, optionally wholly implanted in the patient.

In certain embodiments, the modulation in neural activity as a result of applying the signal is an increase in neural activity in the nerve to which the signal is applied. In certain embodiments, the signal is an electrical signal and comprises a low frequency alternating current (AC) waveform, optionally having a frequency of 0.01-20 Hz, for example 10 Hz.

In certain embodiments, the method further comprises the step of detecting one or more physiological parameters of the patient, wherein the signal is applied only when the detected physiological parameter meets or exceeds a predefined threshold value. In certain such embodiments, one or more detected physiological parameters is selected from: sympathetic tone; gut tissue and/or circulating nor-epinephrine (NE) levels; gut tissue and/or circulating substance P levels; gut tissue and/or circulating levels of one or more inflammatory markers. In certain embodiments the one or more detected physiological parameters comprise an action potential or pattern of action potentials in a nerve of the patient.

In another aspect, the invention provides an anti-inflammatory agent for use in a method of treating colitis in a patient, wherein the method comprises: (i) applying a signal to the splenic nerve (or any nerve that innervates the spleen) and/or the superior mesenteric plexus of the patient to modulate the neural activity in the nerve in the patient; and (ii) administering the anti-inflammatory agent to the patient. In certain embodiments, the anti-inflammatory agent is selected from a steroid, a 5-ASA, methotrexate, azathioprine, cyclosporine, and an anti-TNF agent. In certain embodiments, the anti-inflammatory agent is for use in a method of treating IBD, optionally UC and/or Crohn's Disease.

In certain embodiments, the signal or signals are applied by a neuromodulation device comprising a transducer configured to apply each signal, optionally wherein the neuromodulation device is at least partially implanted in the patient, optionally wholly implanted in the patient.

In certain embodiments, the signal or signals applied increase neural activity in the nerve to which it is applied. In certain embodiments, the signal is an electrical signal, optionally a low frequency AC waveform, optionally having a frequency of 0.01-20 Hz, for example 10 Hz.

In another aspect, the invention provides a neuromodulatory electrical waveform for use in treating colitis in a patient, wherein the waveform is an AC waveform having a frequency of 0.01-20 Hz, such that, when applied to a splenic nerve or SMP the waveform increases neural signalling in the nerve.

In another aspect, the invention provides use of a neuromodulation device for treating colitis in a patient by modulating neural activity in a splenic nerve or SMP of the patient.

In a preferred embodiment of all aspects of the invention, the patient is a mammalian patient, optionally a human patient.

B) Colon weight, normalised for colon length, was measured as indication of colitis.

C-F) Endoscopic pathology score shown as the sum of the clinical disease characteristics. Stool was measured from 0 (normal faeces) to 4 (bloody diarrhoea Histological characteristics evaluated by an experienced pathologist. The sum pathology score is calculated from the different characteristics, also shown as separate graphs. Infiltrate, hyperplasia, Goblet cell depletion are shown.

G) Ileal norepinephrine (NE) was measured with mass spectrometry. It is measured in picogram per total tissue weight in grams. The basal norepinephrine levels of Rag1−/− mice sham surgery compared to Sx.

For panels A-G: data are representative for 2 independent experiments. The sample means plus the SEM are indicated. A Mann-Withney U test (or a Chi Square test for Stool, Endoscopy and all histological characteristics) was used for statistical analysis, *P<0.05, P<0.01, *P<0.001, n=17 for mice receiving Sx and n=16 for mice receiving a sham operation (−).

Figure 5:
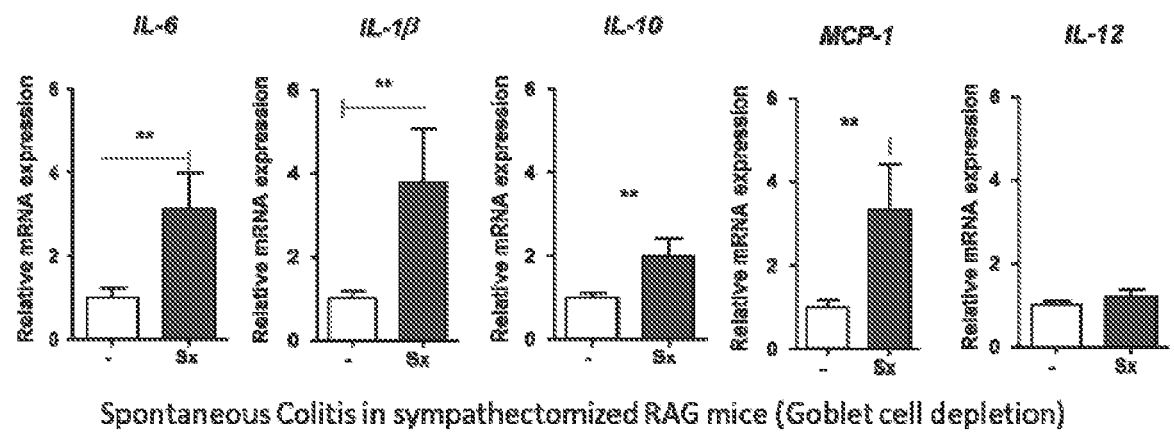
Figure 5:
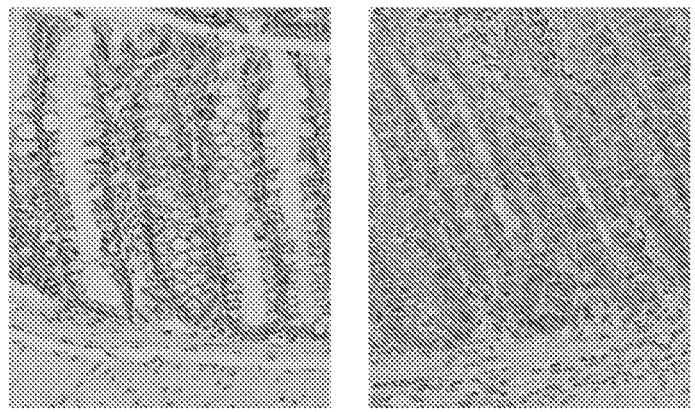

FIG. 5: qPCR analysis of the genes for tumour necrosis factor (TNF)-α, interleukin (IL)1β, IL-6, IL-10, IL-12 and monocyte chemoattractant protein (MCP)-1. Normalised for the housekeeping genes β-actin, hypoxanthine-guanine phosphoribosyltransferase (HPRT) and ubiquitin. Shown as relative mRNA expression related to the sham operated mice (−).

B) Two representative H&E stainings of sham (left) and Sx (Right). Lower arrows: infiltrate, Upper arrows: goblet cell depletion, Magnification: 20×.

Figure 6A:
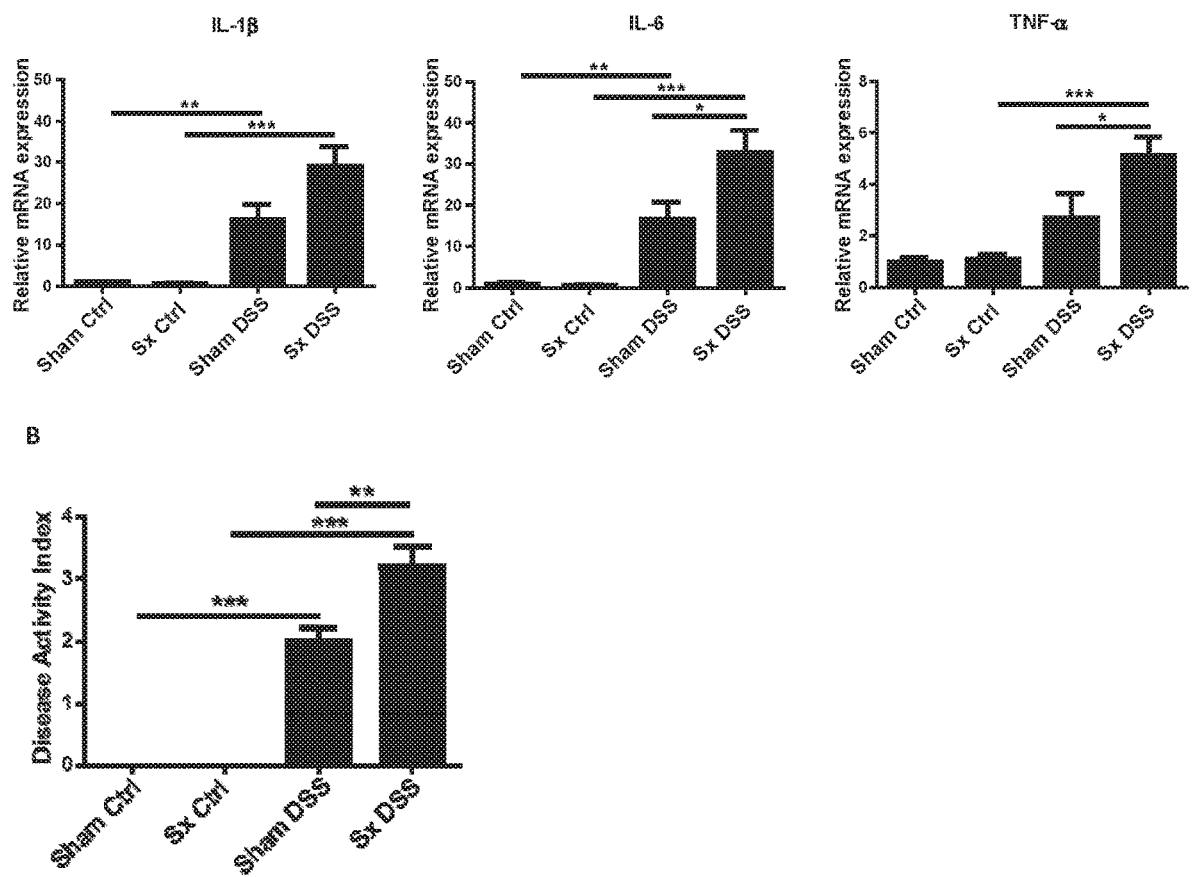

FIG. 6: C57BL/6 mice underwent a sham operation (−), transection of the splenic nerve (Sx). After two weeks of recovery, acute colitis was induced by giving 2% (w/v) DSS in the drinking water, or vehicle as a control.

A) qPCR analysis of the genes for IL-1β, IL-6, IL-10, transforming growth factor (TGF)-β and TNF-α. Normalised for the housekeeping genes β-actin, HPRT and ubiquitin. Shown as relative mRNA expression related to the sham operated mice treated with vehicle.

B) Disease activity index was measured as indication of disease. Fibrosis is included as measure for disease activity as a macroscopic score from 0 (no fibrosis) to 2 (severe fibrosis). Stool was measured from 0 (normal faeces) to 4 (bloody diarrhoea). The sample means plus the SEM are indicated. A Mann-Withney U test (or a Chi Square test for Stool, Faecal blood and Fibrosis) was used for statistical analysis, *P<0.05, **P<0.01, n=10 mice for each group (−, Sx, with or without DSS colitis).

Figure 7:
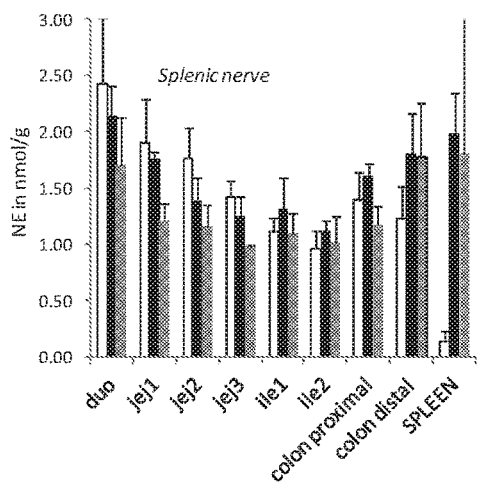
Figure 7:
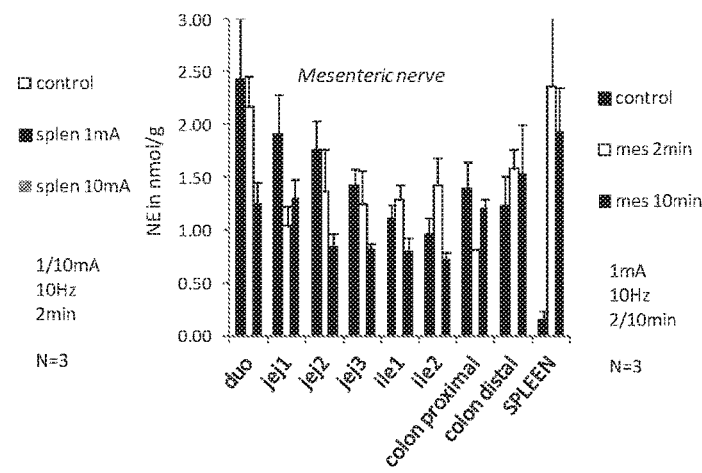

FIG. 7: Norepinephrine (NE) levels of proximal to distal intestinal segments were indicated. NE levels were measured using mass spectrometry. Levels are given in picomole per total tissue weight in grams, taken directly after hook stimulation at indicated parameters. Data shown are averages n=3. Stimulations were performed at indicated parameters.

FIG. 8: Electromyographic recordings at the peritoneal muscle. A cuff electrode was implanted, positioned around the superior mesenteric plexus and superior mesenteric artery. An EMG electrode was then implanted for measurement. Rats underwent a stimulation of A) 200 microAmp 10 Hz stimulus or B) 400 microAmp (at arrow) 10 Hz stimulus and EMG was measured over time as indicated.

Figure 9A:
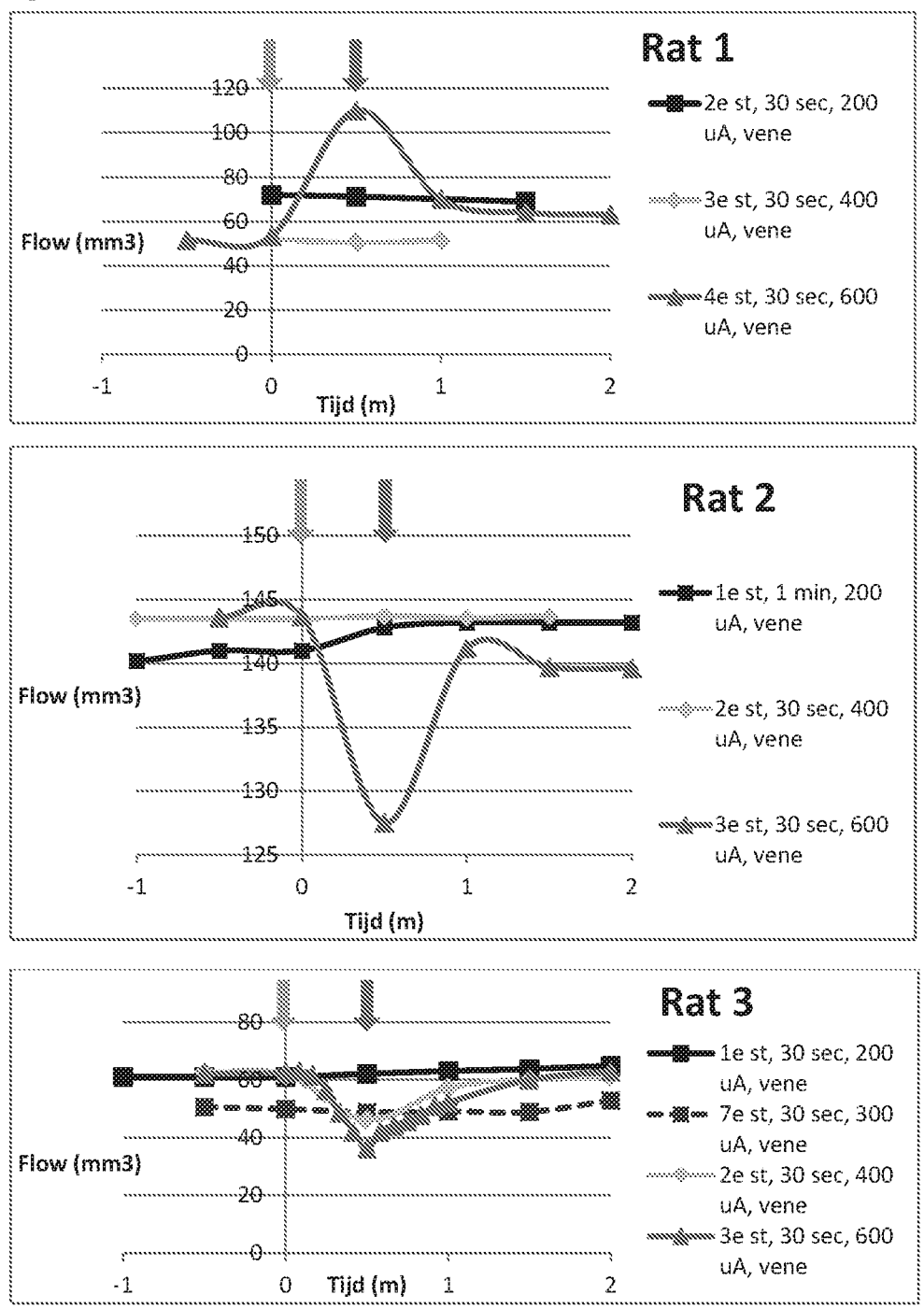
Figure 9B:
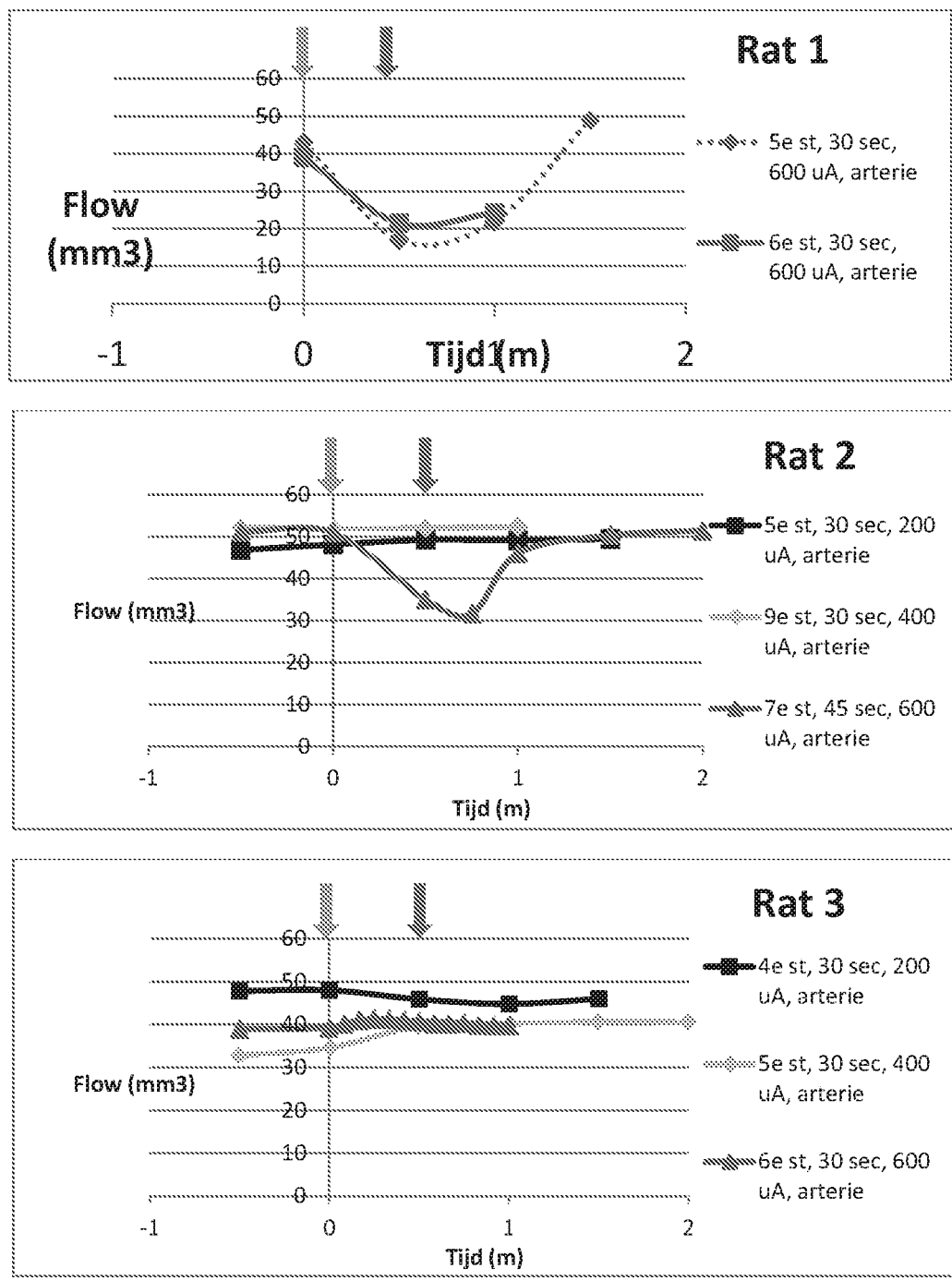

FIG. 9: Rat Doppler circulation flow measurements at venous (A) or arterial (B) mesenteric vessels, after stimulation via a an electrode cuff placed around the superior mesenteric plexus and artery. Measurements of three rats are shown. Stimulation parameters were 200, 400, and 600 microAmp, at 10 Hz stimulus given were D indicated.

Figure 10:
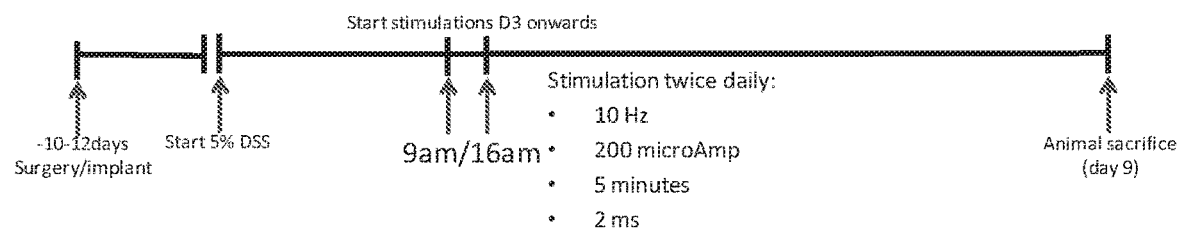

FIG. 10: Protocol details of the experimental rat superior mesenteric plexus (SMP) stimulation procedure FIG. 11: Experimental outcomes of the pilot SMP stimulation in DSS colitis in rat. A) endoscopy micrograph of sham (upper) and stimulated colon at day 9 of DSS colitis. Note the area's of ulceration an fibrosis (arrows). B) colon weight/length ratio measured in rat colons at day 9 of DSS colitis. C) clinical parameters of colitis at day 9 of DSS in rats undergoing sham, or stimulation of SMP as in FIG. 1. parametres measured are diarrhea (black bars) or blood in stool (observed; gray bars). D) transcription of cytokines and chemokines measured in colon homogenates by QPCR. Selected biomarkers are deduced from QPCR array screening (SA Biosciences human inflammation kit) that showed upregulation of CCL3, CCL12, CCL17, IL1b in rat DSS at day 9. Shown are levels of CCL3 and IL-1β under sham, or stimulation, in colon at day 9 of DSS. CCL12, CCL17 were equally reduced (not shown); CCL19 and COX 2 were unaffected by stimulation. Data shown are mean+/−SEM n=7-9 per treatment group.

Figure 12:
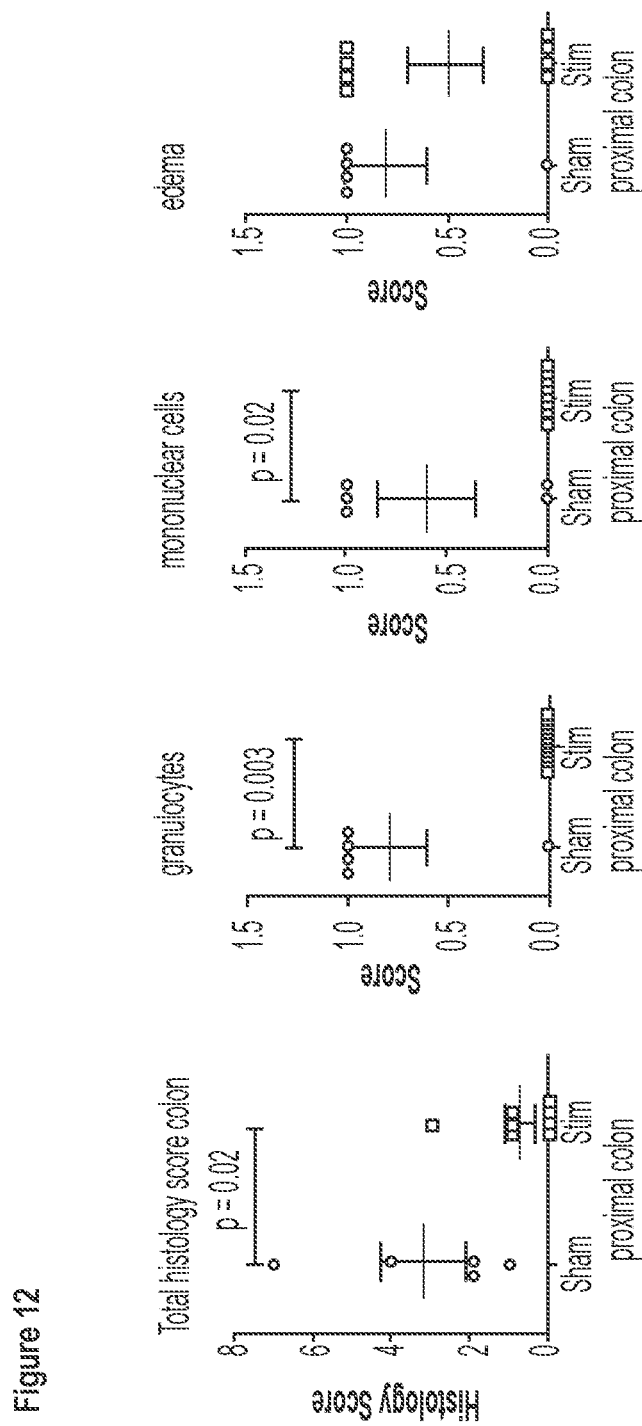

FIG. 12: Histology score-SMP stimulation. Experimental outcomes of the pilot SMP stimulation in DSS colitis in rat. Histology scores as assessed by an experienced and blinded pathologist. Data shown are mean+/−SEM n=7-9 per treatment group.

Figure 13:
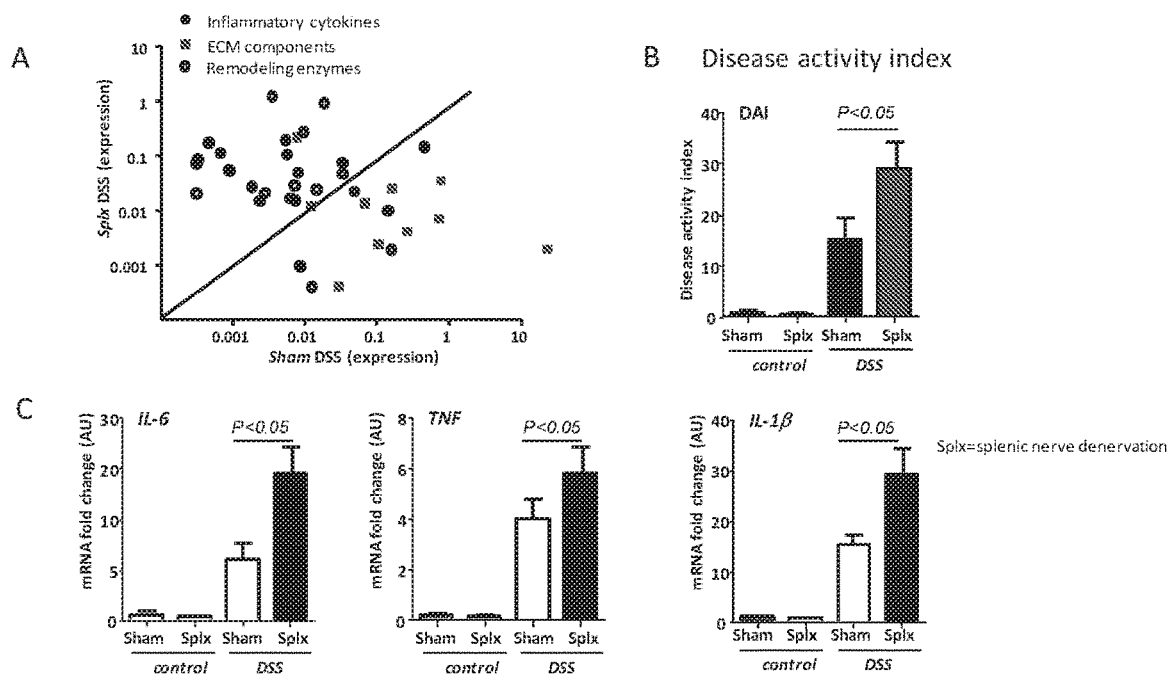

FIG. 13: Sympathetic splenic innervation exerts an anti-inflammatory effect on the DSS-induced colonic inflammation. Spleen denervation performed prior to DSS administration augments DSS colitis in mice. QPCR array data of colon transcripts; elevated expression profiles for inflammatory genes are seen after splx (splenic nerve lesion) as compared to sham surgery. B) splenic nerve lesion leads to enhance in the Disease Activity Index (C) induced by DSS administration, C). Spleen denervation leads to a significant increase in the expression level of the pro-inflammatory cytokines IL-6 and TNF-α as well as of IL-1β. Data are expressed as mean±SEM (n=11-15 animals per group). * $p<0.05$; $p<0.01$; *$p<0.001$. Cytokine expression levels in DSS colitis and splenic nerve denervation (n=12)

DETAILED DESCRIPTION

The terms as used herein are given their conventional definition in the art as understood by the skilled person, unless otherwise defined below. In the case of any inconsistency or doubt, the definition as provided herein should take precedence.

As used herein, application of a signal may equate to the transfer of energy in a suitable form to carry out the intended effect of the signal. That is, application of a signal to a nerve or nerves may equate to the transfer of energy to (or from) the nerve(s) to carry out the intended effect. For example, the energy transferred may be electrical, mechanical (including acoustic, such as ultrasound), electromagnetic (e.g., optical), magnetic or thermal energy. It is noted that application of a signal as used herein does not include a pharmaceutical intervention.

As used herein, "transducer" is taken to mean any element of applying a signal to the nerve or plexus, for example an electrode, diode, Peltier element or ultrasound transducer.

As used herein, a "non-destructive signal" is a signal as defined above that, when applied, does not irreversibly damage the underlying neural signal conduction ability of the nerve to which it is applied. That is, application of a non-destructive signal maintains the ability of the nerve or nerves (or fibres thereof) to conduct action potentials when application of the signal ceases, even if that conduction is in practice inhibited or blocked as a result of application of the non-destructive signal. Ablation and cauterisation of at least part of the nerve are examples of destructive signals.

As used herein, "neural activity" of a nerve is taken to mean the signalling activity of the nerve, for example the amplitude, frequency and/or pattern of action potentials in the nerve.

Modulation of neural activity, as used herein, is taken to mean that the signalling activity of the nerve is altered from the baseline neural activity that is, the signalling activity of the nerve in the patient prior to any intervention. Such modulation may increase, inhibit (for example block), or otherwise change the neural activity compared to baseline activity.

Where the modulation of neural activity is stimulatory (resulting in an increase of neural activity), this may be an increase in the total signalling activity of the whole nerve, or it may be that the total signalling activity of a subset of nerve fibres of the nerve is increased, compared to baseline neural activity in that part of the nerve.

Where the modulation of neural activity is inhibition of neural activity, such inhibition may be partial inhibition. Partial inhibition may be such that the total signalling activity of the whole nerve is partially reduced, or that the total signalling activity of a subset of nerve fibres of the nerve is fully reduced (that is, there is no neural activity in that subset of fibres of the nerve), or that the total signalling of a subset of nerve fibres of the nerve is partially reduced compared to neural activity in that subset of fibres of the nerve prior to intervention. Where the modulation of neural activity is inhibition of neural activity, this also encompasses full inhibition of neural activity in the nerve.

Inhibition of neural activity may be a block on neural activity. Such blocking may be a partial block—that is, blocking of neural activity in a subset of nerve fibres of the nerve. Alternatively, such blocking may be a full block—i.e., blocking of neural activity across the whole nerve. A block on neural activity is understood to be blocking neural activity from continuing past the point of the block. That is, when the block is applied, action potentials may travel along the nerve or subset of nerve fibres to the point of the block, but not beyond the block.

Modulation of neural activity may also be an alteration in the pattern of action potentials. It will be appreciated that the pattern of action potentials can be modulated without necessarily changing the overall frequency or amplitude. For example, modulation of the neural activity may be such that the pattern of action potentials is altered to more closely resemble a healthy state rather than a disease state.

Modulation of neural activity may comprise altering the neural activity in various other ways, for example increasing or inhibiting a particular part of the neural activity and/or stimulating new elements of activity, for example in particular intervals of time, in particular frequency bands, according to particular patterns and so forth. Such altering of neural activity may for example represent both increases and/or decreases with respect to the baseline activity.

Modulation of the neural activity may be temporary. As used herein, "temporary" is taken to mean that the modulated neural activity (whether that is an increase, inhibition, block or other modulation of neural activity or change in pattern versus baseline activity) is not permanent. That is, the neural activity following cessation of the signal is substantially the same as the neural activity prior to the signal being applied—i.e., prior to modulation. Neural activity prior to modulation is referred to herein as "baseline" activity.

Modulation of the neural activity may be persistent. As used herein, "persistent" is taken to mean that the modulated neural activity (whether that is an increase, inhibition, block or other modulation of neural activity or change in pattern versus baseline activity) has a prolonged effect. That is, upon cessation of the signal, neural activity in the nerve remains substantially the same as when the signal was being applied (that is, the neural activity during and following modulation is substantially the same). The prolonged effect may be temporary, as described above, such that after a period of time (e.g., minutes, for example 30 minutes or more, or hours, or even days) following cessation of the signal, the neural activity returns to baseline, or the prolonged effect may continue indefinitely or permanently.

Modulation of the neural activity may be corrective. As used herein, "corrective" is taken to mean that the modulated neural activity (whether that is an increase, inhibition, block or other modulation of neural activity or change in pattern versus baseline activity) alters the neural activity towards the pattern of neural activity in a healthy individual. That is, upon application (and/or following cessation) of the signal, neural activity in the nerve more closely resembles the pattern of action potentials in the nerve observed in a healthy subject than prior to modulation, preferably substantially fully resembles the pattern of action potentials in the nerve observed in a healthy subject.

Such corrective modulation caused by the signal can be any modulation as defined herein. For example, application of the signal may result in a change in neural activity, and upon cessation of the signal, the pattern of action potentials in the nerve resembles the pattern of action potentials observed in a healthy subject. By way of further example, application of the signal may result in modulation such that the neural activity resembles the pattern of action potentials observed in a healthy subject, and upon cessation of the signal, the pattern of action potentials in the nerve resembles the pattern of action potentials observed in a healthy individual.

As used herein, the "superior mesenteric plexus" is taken to refer to the plexus of neural fibres associated with the mesenteric artery. The splenic nerve refers to the nerve innervating the spleen as understood by the skilled person.

As used herein, "colitis" is used to refer to inflammation of the colon, in particular mucosal inflammation. Disorders causing colitis include inflammatory bowel disease (including ulcerative colitis (UC) and Crohn's disease), ischaemic colitis, and infectious colitis. Colitis may be associated with infection, autoimmunity, and/or pharmacological action (e.g., through use of non-steroidal anti-inflammatory drugs (NSAIDs)).

"Inflammatory bowel disease (IBD)", as used herein, encompasses UC and Crohn's disease. Crohn's disease and UC are each chronic relapsing and remitting inflammatory diseases characterised by the symptoms including but not limited to abdominal swelling, cramping, pain or discomfort, diarrhoea, weight loss, rectal bleeding and fatigue and may also include anemia, vomiting and elevated temperature (fever). Crohn's disease can affect any part of the gastrointestinal (GI) tract, for example the colon, and is characterised by patchy, transmural and mucosal inflammation. In UC, the inflammation is continuous, extending proximally from the rectum and generally limited to the colon.

"Treatment of colitis"—as used herein, "treatment of colitis" is characterised by a reduction in one or more symptoms exhibited by the patient suffering from the colitic disorder. For example, treatment may be characterised by any one or more of a decrease in gut pathology (for example as measured by endoscopy and/or histology, e.g., crypt loss, polyps, hyperplasia, goblet cell depletion), a decrease in colon fibrosis, a reduction in one or more of abdominal swelling, cramping pain or discomfort, diarrhoea, vomiting, fever, weight loss, rectal bleeding, anemia and fatigue. Such a reduction in a symptom may be characterised by the symptom being less frequent, or less severe, or both.

Treatment may be prophylactic or therapeutic. Prophylactic treatment may be characterised by the prevention of onset of symptoms. For example, colitis patients can go through periods of remission between symptomatic episodes or crises. Prophylactic treatment may prevent onset of further episodes or extend periods of remission. Therapeutic treatment may be characterised by amelioration of an ongoing episode of colitis. For example, therapeutic treatment may result in amelioration of the frequency and/or severity of symptoms during an episode, or cause the patient to enter a state of remission. Therapeutic treatment may entirely cure the patient of colitis.

As used herein, an "improvement in a measurable physiological parameter" is taken to mean that for any given physiological parameter, an improvement is a change in the value of that parameter in the patient towards the normal value or normal range for that value—i.e., towards the expected value in a healthy individual.

For an example, in a patient suffering from colitis, an improvement in a measurable parameter may be one or more of an increase in sympathetic tone, an increase in gut tissue and/or circulating (i.e., blood/plasma) nor-epinephrine, a decrease in one or more inflammatory markers (for example inflammatory cytokines (e.g., TNFα, IL-6, IL-1β, MCP-1, IL-17, C-reactive protein, and calprotectin) in gut tissue and/or circulation, a decrease in gut pathology (for example as measured by endoscopy and/or histology, e.g., crypt loss, polyps, hyperplasia, goblet cell depletion), a decrease in colon fibrosis, and a reduction in one or more symptoms such as abdominal swelling, cramping, pain or discomfort, diarrhoea, weight loss, rectal bleeding, vomiting, anemia, elevated temperature and fatigue.

A suitable physiological parameter may be an action potential or pattern of action potentials in a nerve of the patient. An improvement in such a parameter is characterised by the action potential or pattern of action potentials in the nerve more closely resembling that exhibited by a healthy individual than before the intervention.

As used herein, a physiological parameter is not affected by modulation of the neural activity if the parameter does not change as a result of the modulation from the average value of that parameter exhibited by the subject or patient when no intervention has been performed—i.e., it does not depart from the baseline value for that parameter.

The skilled person will appreciate that the baseline for any neural activity or physiological parameter in an individual need not be a fixed or specific value, but rather can fluctuate within a normal range or may be an average value with associated error and confidence intervals. Suitable methods for determining baseline values would be well known to the skilled person.

As used herein, a measurable physiological parameter is "detected" in a patient when the value for that parameter exhibited by the patient at the time of detection is determined. A detector is any element able to make such a determination.

A "predefined threshold value" for a physiological parameter is the value for that parameter where that value or beyond must be exhibited by a subject or patient before the intervention is applied. For any given parameter, the threshold value may be a value indicative of colitis. Examples of such predefined threshold values include sympathetic tone less than a threshold sympathetic tone, for example the sympathetic tone in a healthy individual; gut tissue and/or circulating nor-epinephrine (NE) levels greater than a threshold NE level, for example the NE level in a healthy individual; gut tissue and/or circulating levels of one or more inflammatory markers (for example, TNFα, IL-6, IL-1β, MCP-1, IL-17, C-reactive protein, calprotectin) greater than that characteristic of a healthy individual. Appropriate values for any given parameter would be simply determined by the skilled person.

Such a threshold value for a given physiological parameter is exceeded if the value exhibited by the patient is beyond the threshold value—that is, the exhibited value is a greater departure from the normal or healthy value for that parameter than the predefined threshold value.

As used herein, sympathetic tone is used to mean the overall physiological balance resulting from sympathetic neural activity. Such sympathetic tone may be determined by methods known in the art, for example neurological methods, hemodynamic methods (e.g., heart rate, blood pressure, heart rate variability) or circulating plasma urine biomarkers.

A "neuromodulation device" as used herein is a device configured to modulate the neural activity of a nerve. Neuromodulation devices as described herein comprise at least one transducer capable of effectively applying a signal to a nerve. In those embodiments in which the neuromodulation device is at least partially implanted in the patient, the elements of the device that are to be implanted in the patient are constructed such that they are suitable for such implantation. Such suitable constructions would be well known to the skilled person. Indeed, various fully implantable neuromodulation devices are currently available, such as the vagus nerve stimulator of SetPoint Medical, in clinical development for the treatment of rheumatoid arthritis (Arthritis & Rheumatism, Volume 64, No. 10 (Supplement), page S195 (Abstract No. 451), October 2012. *"Pilot Study of Stimulation of the cholinergic Anti-Inflammatory Pathway with an Implantable Vagus Nerve Stimulation Device in Patients with Rheumatoid Arthritis"*, Frieda A. Koopman et al), and the INTERSTIM™ device (Medtronic, Inc), a fully implantable device utilised for sacral nerve modulation in the treatment of overactive bladder. In certain embodiments, the neuromodulation device, or implantable portion of an apparatus or system, can be miniaturized to a size of less than 1 cm.

As used herein, "implanted" is taken to mean positioned at least partially within the patient's body. Partial implantation means that only part of the device (or apparatus or system) is implanted—i.e., only part of the device is positioned within the patient's body, with other elements of the device external to the patient's body. The term "wholly implanted" means that the entire of the device is positioned within the patient's body. For the avoidance of doubt, the device being "wholly implanted" does not preclude additional elements, independent of the device but in practice useful for its functioning (for example, a remote wireless charging unit or a remote wireless manual override unit), being independently formed and external to the patient's body.

As used herein, "charge-balanced" in relation to a current (e.g., a DC current) is taken to mean that the positive or negative charge introduced into any system (e.g., a nerve) as a result of the current being applied is balanced by the introduction of the opposite charge in order to achieve overall (i.e., net) neutrality.

As shown herein, it has been identified that colitis can be relieved and/or prevented by modulation of the neural activity of the splenic nerve and/or in the superior mesenteric plexus.

Previous investigations relating to treatment of IBD have focussed on stimulation of the vagus nerve (sometimes referred to as the vagal nerve), in particular the left cervical vagus, which was thought to mediate an anti-inflammatory effect via cholinergic (i.e., parasympathetic) signalling. Surprisingly, however, it is shown herein that sympathetic (i.e., adrenergic) neural signalling to the gut is required for an anti-inflammatory response in a colitis model. In particular, sympathetic signalling to the gut from the coeliac ganglion via either the splenic nerve or SMP, or both, is shown to play a role in moderating the severity of colitis. This is contrast to previous hypotheses which postulated direct parasympathetic vagal signalling to the gut as the mechanism by which any anti-inflammatory effect was mediated. Moreover, the present inventors have shown that such sympathetic signalling to the gut also mediates an anti-inflammatory effect independent from that of the vagus nerve.

It is further demonstrated herein that modulation of the neural activity in one or both of the splenic nerve (or any nerve that innervates the spleen) and the SMP will be able to relieve colitis. Throughout this disclosure, where the splenic nerve is referenced, the reference should be understood to encompass any sympathetic nerve that innervates the spleen. By modulating the neural activity of nerves more distal from and more specifically associated with the gut than the vagus nerve, the present invention is able to treat colitis without the risk of unwanted side-effects often associated with vagus nerve stimulation (sometimes referred to as vagal nerve stimulation, as used herein the terms vagus nerve and vagal nerve may be used interchangeably).

A neuromodulation device that modulates the neural activity of the splenic nerve and/or SMP will therefore provide an effective colitis treatment.

Therefore, this disclosure provides an apparatus or system for modulating the neural activity of the splenic nerve and/or the SMP of a patient, the apparatus or system comprising: a first transducer configured to apply a first signal to the splenic nerve or SMP and optionally a second transducer to apply a second signal to the other of the SMP or splenic nerve; and a controller coupled to the transducer or transducers, the controller controlling the signal to be applied by the transducer or transducers, such that the signal modulates the neural activity of the nerve to which it is applied (i.e., the splenic nerve and/or the SMP, as appropriate) to produce a physiological response in the patient.

In those embodiments in which the apparatus or system has at least two transducers, the signal that each of the transducers is configured to apply is independently selected. In certain embodiments each transducer is configured to apply the same signal.

The following description and embodiments of the signal apply to any signal applied by the device i.e., may apply independently to the first and second signals, and any further signals applied by the device.

In certain embodiments, the signal applied by the one or more transducers is a non-destructive signal.

In certain such embodiments, the signal applied by the one or more transducers is an electrical signal, an optical signal, an ultrasonic signal, or a thermal signal.

In certain embodiments, each of the one or more transducers may be comprised of one or more electrodes, one or more photon sources, one or more ultrasound transducers, one more sources of heat, or one or more other types of transducer arranged to put the signal into effect.

In certain embodiments, the signal or signals applied by the one or more transducers is an electrical signal, for example a voltage or current. In certain such embodiments the signal applied comprises a direct current (DC) waveform, such as a charge balanced direct current waveform, or an alternating current (AC) waveform, or both a DC and an AC waveform.

In certain embodiments, the electrical signal comprises a square waveform, a sinusoidal waveform, a saw-toothed waveform or a triangular waveform. In certain preferred embodiments, the signal has a square waveform.

In certain embodiments the electrical signal comprises a low frequency AC waveform. In certain embodiments, the electrical signal is an AV waveform having a frequency of 0.01 Hz-1 kHz, 0.01-900 Hz, 0.01-800 Hz, 0.01-700 Hz, 0.01-600 Hz, 0.01-500 Hz, 0.01-400 Hz, 0.01-300 Hz, 0.01-200 Hz, 0.01-100 Hz, 0.01-50 Hz. In certain such embodiments the signal comprises an AC waveform having a frequency of 0.01-20 Hz, preferably 0.5-20 Hz, for example 1-15 Hz, preferably 5-10 Hz. In certain embodiments, the signal comprises an AC waveform having a frequency of 0.01 Hz, 0.05 Hz, 0.1 Hz, 0.5 Hz, 1 Hz, 2 Hz, 3 Hz, 4 Hz, 5 Hz, 6 Hz, 7 Hz, 8 Hz, 9 Hz or 10 Hz, such as 10 Hz.

In certain embodiments, the electrical signal has a current of 0.1-20 mA, 0.1-10 mA, 0.1-5 mA, 0.1-3 mA, 0.1-1 mA, 0.1-0.5 mA, 0.16 mA-0.6 mA, 0.2-0.4 mA, for example 0.2-0.4 mA. In certain embodiments the electrical signal has a current of at least 0.16 mA. In certain embodiments, the electrical signal has a current of 0.1 mA, 0.15 mA, 0.16 mA, 0.18 mA, 0.2 mA, 0.2 mA, 0.4 mA, 0.6 mA, 1 mA, 2 mA, 3 mA, 5 mA, 10 mA, such as 0.2 mA.

In certain embodiments the electrical signal has a pulse width of 20-500 microseconds (µs). In certain embodiments the signal has a pulse width of 20-500 µs, 30-400 µs, 40-300 µs, 50-200 µs, 60-150 µs, 70-120 µs, 80-100 µs.

In certain embodiments, the electrical signal comprises a DC waveform and/or an AC waveform having a voltage of 0.1-20V. In certain preferred embodiments, the signal has a voltage of 0.1-15V, optionally 0.1-10V. In certain preferred embodiments the voltage is selected from 0.1V, 0.2V, 0.3V, 0.5V, 0.6V, 0.7V, 0.8V, 0.9V, 1V, 2V, 3V, 5V and 10V.

In certain exemplary embodiments, the electrical signal comprises an AC square biphasic waveform of 10 Hz 0.2 mA.

As will be appreciated by the skilled person, the current or voltage of a signal can be varied in order to achieve the intended value of the other parameter for any given device-nerve arrangement.

In certain embodiments the signal comprises a DC ramp followed by a plateau and charge-balancing, followed by a first AC waveform, wherein the amplitude of the first AC waveform increases during the period in which the first AC waveform is applied, followed by a second AC waveform having a lower amplitude and/or lower frequency than the first AC waveform. In certain such embodiments, the DC ramp, first AC waveform and second AC waveform are applied substantially sequentially.

In certain embodiments, the signal comprises an AC waveform of kilohertz frequency. In certain embodiments, wherein the signal comprises one or more AC waveforms, each AC waveform is independently selected from an AC waveform of 5-25 kHz, optionally 10-25 kHz, optionally 15-25 kHz, optionally 20-25 kHz. In certain embodiments, the signal comprises an AC waveform signal of S kHz. In certain alternative embodiments, the signal comprises an AC waveform of 25 kHz.

In those embodiments in which the signal applied is an electrical signal, at least one of the one or more transducers is an electrode configured to apply the electrical signal. In certain such embodiments, all the transducers are electrodes configured to apply an electrical signal, optionally the same electrical signal.

In certain embodiments in which the signal applied is an electrical signal, the signal is applied by a cuff electrode. In certain such embodiments, the cuff is configured to encompass the nerve to which the signal is applied and optionally the associated blood vessel. For example, in certain embodiments in which an electrical signal is applied to the SMP, the signal is applied by a cuff electrode configured to encompass the SMP and the superior mesenteric artery.

In certain embodiments wherein the signal applied is a thermal signal, the signal reduces the temperature of the nerve (i.e., cools the nerve). In certain alternative embodiments, the signal increases the temperature of the nerve (i.e., heats the nerve). In certain embodiments, the signal both heats and cools the nerve.

In those embodiments in which the signal applied is a thermal signal, at least one of the one or more transducers is a transducer configured to apply a thermal signal. In certain such embodiments, all the transducers are configured to apply a thermal signal, optionally the same thermal signal.

In certain embodiments, one or more of the one or more transducers comprise a Peltier element configured to apply a thermal signal, optionally each of the one or more transducers comprises a Peltier element. In certain embodiments, one or more of the one or more transducers comprise a laser diode configured to apply a thermal signal (e.g., a near infrared (NIR) diode laser), optionally all of the one or more transducers comprise a laser diode configured to apply a thermal signal. In certain embodiments, one or more of the one or more transducers comprise a electrically resistive element configured to apply a thermal signal, optionally each of the one or more transducers comprises a electrically resistive element configured to apply a thermal signal.

In certain embodiments the signal applied is a mechanical signal, optionally an ultrasonic signal. In certain alternative embodiments, the mechanical signal is a pressure signal.

In certain embodiments the signal is an electromagnetic signal, optionally an optical signal. In certain such embodiments, the one or more transducers comprise a laser and/or a light emitting diode (e.g., an NIR diode laser) configured to apply the optical signal. In some embodiments, the apparatus or system further comprises a fibre optic interface configured to apply the signal from the one or more of the transducers to the at least one nerve.

In certain embodiments, the physiological response produced in the patient is one or more of an increase in sympathetic tone, an increase in gut tissue and/or circulating/plasma nor-epinephrine, a decrease in one or more inflammatory markers (for example inflammatory cytokines (e.g., TNFα, IL-6, IL-1β, MCP-1, IL-17, C-reactive protein and calprotectin) in gut tissue and/or plasma, a change in blood flow or circulation through the colon and/or spleen, a decrease in gut pathology (for example as measured by endoscopy and/or histology, e.g., crypt loss, polyps, hyperplasia, goblet cell depletion), a decrease in colon fibrosis, and a reduction in one or more symptoms such as abdominal swelling, cramping, pain or discomfort, diarrhoea, weight loss, rectal bleeding, vomiting, anemia, elevated temperature and fatigue.

In certain embodiments, the physiological response produced in the patient may be an improvement in the pattern of action potentials in a nerve of the patient—that is the pattern of action potentials in the nerve more closely resembles that exhibited by a healthy individual than before the intervention. In certain such embodiments the nerve is the splenic nerve, the SMP or the vagus nerve.

In certain embodiments, the apparatus or system further comprises a detector element to detect one or more physiological parameters in the patient. Such a detector element may be configured to detect the one or more physiological parameters. That is, in such embodiments each detector may detect more than one physiological parameter, for example all the detected physiological parameters. Alternatively, in such embodiments each of the one or more detector elements is configured to detect a separate parameter of the one or more physiological parameters detected.

In such certain embodiments, the controller is coupled to the detector element configured to detect one or more physiological parameters, and causes the transducer or transducers to apply their respective signal when the physiological parameter is detected to be meeting or exceeding a predefined threshold value.

In certain embodiments, the one or more detected physiological parameters are one or more of sympathetic tone; gut tissue and/or circulating nor-epinephrine (NE) levels; gut tissue and/or circulating substance P levels; gut tissue and/or circulating levels of one or more inflammatory markers (for example, TNFα, IL-6, IL-1β, MCP-1, IL-17, calprotectin).

In certain embodiments, the one or more detected physiological parameters may include an action potential or pattern of action potentials in a nerve of the patient, wherein the action potential or pattern of action potentials is associated with colitis. In certain such embodiments, the nerve is the splenic nerve or SMP. In certain embodiments, the action potential or pattern of action potentials is detected in the vagus nerve, for example the afferent fibres of the vagus nerve.

It will be appreciated that any two or more of the indicated physiological parameters may be detected in parallel or consecutively. For example, in certain embodiments, the controller is coupled to a detector or detectors configured to detect the pattern of action potentials in the SGM and also the heart rate variability of the patient as an indication of sympathetic tone.

In certain embodiments, the modulation in neural activity as a result of applying the signal is an increase in neural activity in the nerve to which the signal is applied. That is, in such embodiments, application of the signal results in the neural activity in at least part of the nerve being increased compared to the baseline neural activity in that part of the nerve. Such an increase in activity could equally be across the whole nerve. Therefore, in certain such embodiments, a result of applying the signal is an increase in neural activity across the whole nerve. Treatment of colitis is expected to be particularly effective when sympathetic signalling by one or both of the splenic nerve or SMP is increased.

In certain embodiments, the signal applied to increase neural activity is an electrical signal comprising an AC waveform of low frequency. In certain embodiments the electrical signal comprises a low frequency AC waveform. In certain embodiments, the electrical signal is an AV waveform having a frequency of 0.01 Hz-1 kHz, 0.01-900 Hz, 0.01-800 Hz, 0.01-700 Hz, 0.01-600 Hz, 0.01-500 Hz, 0.01-400 Hz, 0.01-300 Hz, 0.01-200 Hz, 0.01-100 Hz, 0.01-50 Hz. In certain such embodiments the signal comprises an AC waveform having a frequency of 0.01-20 Hz, for example 0.5-20 Hz, 1-15 Hz, 5-10 Hz. In certain embodiments, the signal comprises an AC waveform having a frequency of 0.01 Hz, 0.05 Hz, 0.1 Hz, 0.5 Hz, 1 Hz, 2 Hz, 3 Hz, 4 Hz, 5 Hz, 6 Hz, 7 Hz, 8 Hz, 9 Hz or 10 Hz, for example 10 Hz.

In certain embodiments, the electrical signal has a current of 0.1-20 mA, 0.1-10 mA, 0.1-5 mA, 0.1-3 mA, 0.1-1 mA, 0.1-0.5 mA, 0.16 mA-0.6 mA, 0.2-0.4 mA, for example 0.2-0.4 mA. In certain embodiments the electrical signal has a current of at least 0.16 mA. In certain embodiments, the electrical signal has a current of 0.1 mA, 0.15 mA, 0.16 mA, 0.18 mA, 0.2 mA, 0.2 mA, 0.4 mA, 0.6 mA, 1 mA, 2 mA, 3 mA, 5 mA, 10 mA, such as 0.2 mA.

In certain embodiments, the electrical signal has a square waveform, a sinusoidal waveform, a saw-toothed waveform or a triangular waveform. In certain embodiments, the signal has a square waveform.

In certain embodiments the electrical signal has a pulse width of 20-500 microseconds (μs). In certain embodiments the signal has a pulse width of 20-500 μs, 30-400 μs, 40-300 μs, 50-200 μs, 60-150 μs, 70-120 μs, 80-100 μs.

In certain embodiments, the electrical signal comprises a DC waveform and/or an AC waveform having a voltage of 0.1-20V. In certain preferred embodiments, the signal has a voltage of 0.1-15V, optionally 0.1-10V. In certain embodiments the voltage is selected from 0.1V, 0.2V, 0.3V, 0.5V, 0.6V, 0.7V, 0.8V, 0.9V, 1V, 2V, 3V, 5V and 10V.

In certain exemplary embodiments, the electrical signal comprises an AC square biphasic waveform of 10 Hz 0.2 mA.

In certain embodiments, the modulation in neural activity as a result of applying the signal is an alteration to the pattern of action potentials in the nerve. In certain such embodiments, the neural activity is modulated such that the resultant pattern of action potentials in the nerve more closely resembles the pattern of action potentials in the nerve or nerves observed in a healthy subject than prior to the signal being applied.

In certain embodiments the modulation in neural activity as a result of applying the signal is inhibition of neural activity in the part of the nerve to which the signal is applied. That is, in such embodiments, application of the signal results in the neural activity being reduced compared to the neural activity in that part of the nerve prior to the signal being applied.

Modulation of neural activity may comprise altering the neural activity in various other ways, for example increasing or inhibiting a particular part of the activity and stimulating new elements of activity, for example in particular intervals of time, in particular frequency bands, according to particular patterns and so forth. Such altering of neural activity may for example represent both increases and/or decreases with respect to the baseline activity.

In certain embodiments, the controller causes the signal to be applied intermittently. In certain such embodiments, the controller causes the signal to applied for a period of time (e.g., a first time period), then stopped for a second or immediately subsequent time period, then reapplied and stopped in an alternating pattern, e.g., applied for a third time period, then stopped for a fourth time period. In such an embodiment, the alternating periods of signal application and cessation (e.g., first, second, third and fourth periods, etc.) run sequentially and consecutively. The series of first, second, third and fourth periods (etc.) amounts to one application cycle. In certain such embodiments, multiple application cycles can run consecutively such that the signal is applied in phases, between which phases no signal is applied.

In such embodiments, the duration of the first, second, third and fourth time periods can be independently selected. That is, the duration of each time period may be the same or different any of the other time periods. In certain such embodiments, the duration of each of the first, second, third and fourth time periods is any time from 5 seconds (5 s) to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h (or any combination of such lower and upper limits). In certain embodiments, the duration of each of the (e.g., first, second, third and fourth) time periods is 5 s, 10 s, 30 s, 60 s, 2 min, 5 min, 10 min, 15 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h (or any time period within the limits of a preceding time period).

In certain preferred embodiments, the alternating period of signal application (e.g., first and third time periods, etc.) is from 1 minute to 1 hour, such as 1-20 minutes, 1-10 minutes, 2-10 minutes, for example 2 minutes, or 5 minutes, or 10 minutes, or 20 minutes, or 30 minutes or an hour (or any period in between). In certain such embodiments, the alternating period of signal cessation (e.g., second and fourth time periods, etc.) are from 1-20 minutes, 1-10 minutes, 2-10 minutes, for example 2 minutes, or 5 minutes, or 10 minutes. In certain such embodiments, the signal is applied up to 6 times per day, up to 4 times per day, up to 3 times per day, 2 times per day, once per day. In certain such embodiments, the signal is not applied during alternating periods that are independently selected from 24 hours, 12 hours, 8 hours, and 6 hours (or selected to be of such duration from which the duration of the alternating period during which signal is applied, such that a diurnal repeating pattern is created and maintained). In certain such embodiments, the second and fourth periods comprise the remainder of a period of 24 hours, once the first and third periods, cumulatively, have been subtracted from 24 hours. That is, where the first and third period are, by way of example, 5 minutes each in duration (10 minutes total), the second and third periods comprise 23 hours and 40 minutes in total, that is 11 hours and 50 minutes each. Optionally in such embodiments, the first and second time periods, cumulatively, are a period of 12 hours, and the third and fourth time periods, cumulatively, are a period of 12 hours.

In certain embodiments wherein the controller causes the signal to be applied intermittently, the signal is applied for a specific amount of time per day, or a specific amount of time, twice a day. In certain such embodiments, the signal is applied for at least 2 min, at least 5 min, at least 10 min, at least 20 min, at least 30 min, at least 40 min, at least 50 min, at least 60 min, at least 90 min, at least 2 h, at least 3 h, at least 4 h, at least 5 h, at least 6 h, at least 7 h, at least 8 h, at least 9 h, at least 10 h, at least 11 h, at least 12 h, at least 13 h, at least 14 h, at least 15 h, at least 16 h, at least 17 h, at least 18 h, at least 19 h, at least 20 h, at least 21 h, at least 22 h, at least 23 h per day. In certain such embodiments, the signal is applied continuously for the specified amount of time. In certain alternative such embodiments, the signal may be applied discontinuously across the day, provided the total time of application amounts to the specified time. In a particular embodiment, the signal is applied for 2 min, 5 min, 10 min, 15 min, 20 min, 30 min, 45 min or 60 min, twice a day or four times a day.

In certain embodiments wherein the controller causes the signal to be applied intermittently, the signal is applied only when the patient is in a specific physiological state. In certain such embodiments, the signal is applied only when the patient is experiencing an episode of colitis—i.e., they are experiencing one or more symptoms associated with a colitis crisis or episode, such as abdominal swelling, cramping, pain or discomfort, diarrhoea, weight loss, rectal bleeding, vomiting, anemia, elevated temperature and fatigue. In such embodiments, the status of the patient (e.g., that they are experiencing an episode) can be indicated by the patient. In alternative embodiments, the status of the patient can be detected independently from any input from the patient. In certain embodiments in which the signal is applied by a neuromodulation device, the device further comprises a detector configured to detect the status of the patient, wherein the signal is applied only when the detector detects that the patient is in the specific state. In certain such embodiments, the signal is applied only when the patient is exhibiting an abnormal (e.g., reduced) sympathetic tone.

In certain such embodiments, the apparatus or system further comprises a communication, or input, element via which the status of the patient (e.g., that they are experiencing symptoms of colitis) can be indicated by the patient or a physician. In alternative embodiments, the apparatus or system further comprises a detector configured to detect the status of the patient. Optionally, the signal is applied only when the detector detects that the patient is in the specific state.

In certain alternative embodiments, the controller causes the signal to be permanently applied. That is, once begun, the signal is continuously applied to the nerve or nerves. It will be appreciated that in embodiments wherein the signal is a series of pulses, gaps between pulses do not mean the signal is not continuously applied.

In certain embodiments of the apparatus or system, the modulation in neural activity caused by the application of the signal (whether that is an increase, inhibition, block or other modulation of neural activity) is temporary. That is, upon cessation of the signal, neural activity in the nerve or nerves returns substantially towards baseline neural activity within 1-60 seconds, or within 1-60 minutes, or within 1-24 hours, optionally 1-12 hours, optionally 1-6 hours, optionally 1-4 hours, optionally 1-2 hours. In certain such embodiments, the neural activity returns substantially fully to baseline neural activity. That is, the neural activity following cessation of the signal is substantially the same as the neural activity prior to the signal being applied—i.e., prior to modulation.

In certain alternative embodiments, the modulation in neural activity caused by the application of the signal or signals is substantially persistent. That is, upon cessation of the signal, neural activity in the nerve or nerves remains substantially the same as when the signal was being applied—i.e., the neural activity during and following modulation is substantially the same.

In certain embodiments, the modulation in neural activity caused by the application of the signal is partially corrective, preferably substantially corrective. That is, upon application (and optionally cessation) of the signal, neural activity in the nerve or nerves more closely resembles the pattern of action potentials in the nerve(s) observed in a healthy subject than in the subject prior to modulation, preferably substantially fully resembles the pattern of action potentials in the nerve (s) observed in a healthy subject. In such embodiments, the modulation caused by the signal can be any modulation as defined herein. For example, application of the signal may result in an increase in neural activity, and upon cessation of the signal, the pattern of action potentials in the nerve or nerves resembles the pattern of action potentials observed in a healthy individual. By way of further example, application of the signal may result in modulation such that the neural activity resembles the pattern of action potentials observed in a healthy subject, and upon cessation of the signal, the pattern of action potentials in the nerve or nerves resembles the pattern of action potentials observed in a healthy subject. It is hypothesised that such a corrective effect is the result of a positive feedback loop—that is, the underlying inflammatory state causing the colitis is treated as result of the device and use of the claimed methods, thereby causing the afferent (i.e., sensory) signals from the gut (e.g., afferent vagal signals) to be altered such that the efferent sympathetic-vagal tone is at least partially restored to that of a healthy individual. Such a corrective mechanism may be mediated via an immuno-neuronal reflex.

In certain embodiments, the apparatus or system (or at least one component thereof) is suitable for at least partial implantation into the patient. In certain such embodiments, the apparatus or system (or component thereof) is suitable to be fully implanted in the patient.

In certain embodiments, the apparatus or system further comprises one or more power supply elements, for example a battery, and/or one or more communication elements.

The invention provides a method for treating colitis in a patient, in particular IBD, the method comprising implanting an apparatus or at least one component of a system as described above, positioning the first transducer of the apparatus or system component in signalling contact with the splenic nerve or SMP of the patient, and activating the apparatus or system. In such embodiments, the transducer is in signalling contact with the nerve when it is positioned such that the signal can be effectively applied to the nerve. The apparatus or system is activated when the apparatus or system is in an operating state such that the signal will be applied as determined by the controller.

In certain embodiments, the method comprises positioning a second transducer of the apparatus or system in signalling contact with the SMP or splenic nerve of the patient, whichever is not in signalling contact with the first transducer.

Implementation of all aspects of the invention (as discussed both above and below) will be further appreciated by reference to FIGS. 2A-2C.

Figure 2:
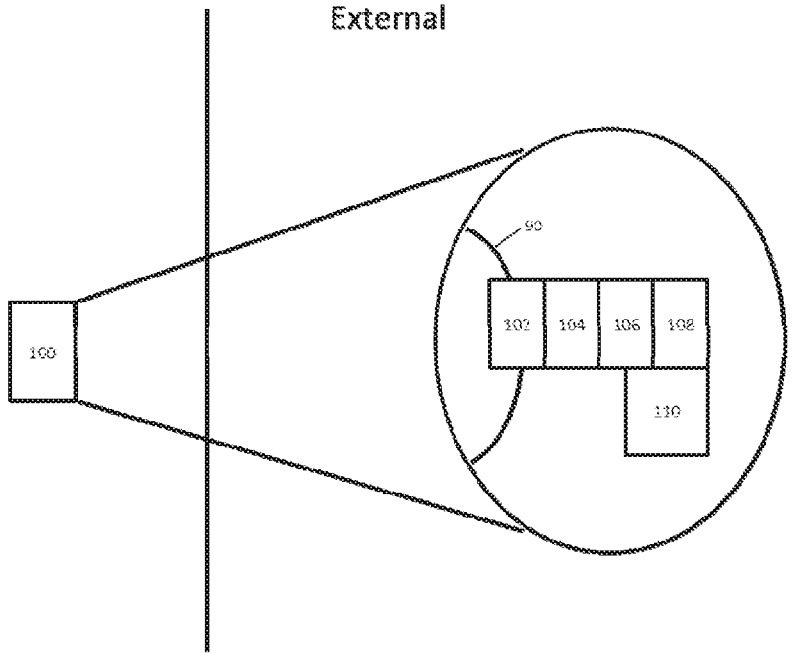
FIG. 2: Schematic drawings showing how apparatuses, devices, systems and methods according to the invention can be put into effect.
Figure 2:
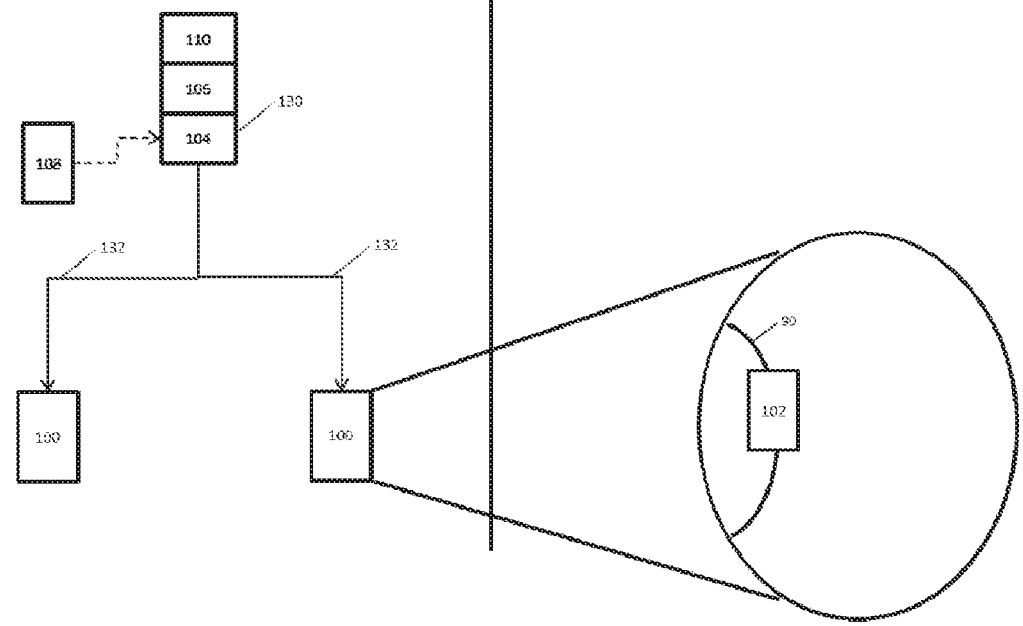
Figure 2C:
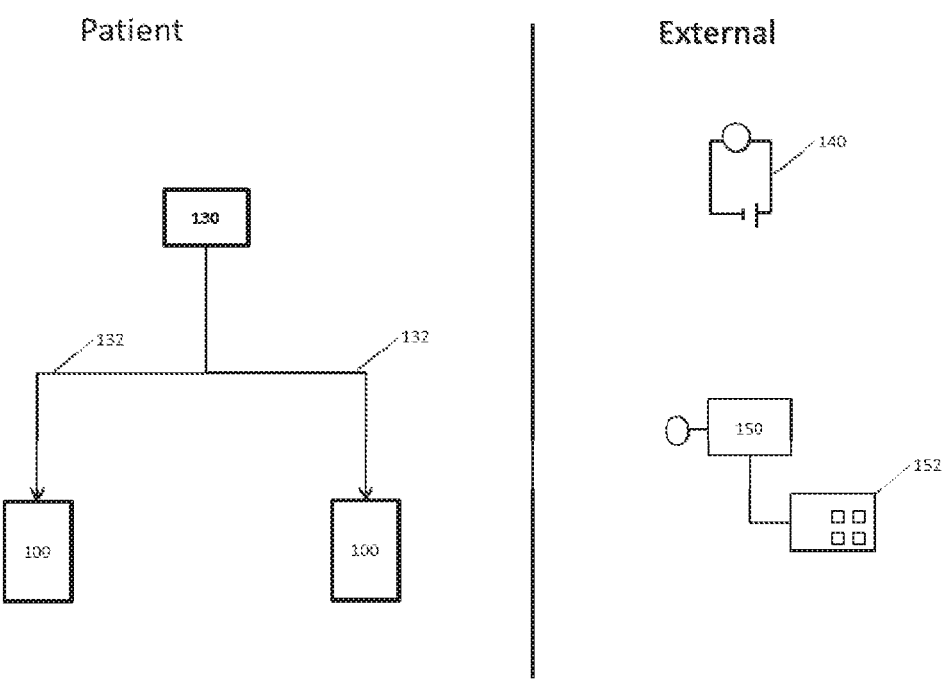

FIGS. 2A-2C show how the invention may be put into effect using one or more neuromodulation devices which are implanted in, located on, or otherwise disposed with respect to a patient in order to carry out any of the various methods described herein. In this way, one or more neuromodulation devices can be used to treat colitis, for example IBD (Crohn's Disease or UC) by modulating neural activity in the splenic nerve and/or SMP of the patient, optionally both the splenic nerve and SMP.

In each of the FIGS. 2B-2C a separate neuromodulation device 100 is provided in respect of each of the splenic nerve and SMP, although as discussed herein a device could be provided or used in respect of only one of the SMP or splenic nerve. Similarly, as discussed herein, one device may be provided or used in respect of both the splenic nerve and SMP—i.e., one device is configured and provided to apply a signal to both nerves.

Each neuromodulation device 100 may be fully or partially implanted in the patient, or otherwise located, so as to provide neuromodulation of the respective nerve or nerves. Each neuromodulation device 100 may operate independently, or may operate in communication with each other.

FIG. 2A also shows schematically components of an implanted neuromodulation device 100, in which the device comprises several elements, components or functions grouped together in a single unit and implanted in the patient. A first such element is a first transducer, preferably an electrode, 102 which is shown in proximity to a splenic nerve or SMP 90 of the patient. As described, device 100 may comprise a second transducer configured for and positioned in proximity to the SMP or splenic nerve, whichever is not in signalling contact with the first transducer (not shown). The transducer 102 may be operated by a controller element 104. The device may comprise one or more further elements such as a communication element 106, a detector element 108, a power supply element 110 and so forth. As described above, transducer 102 may be in the form of a cuff electrode configured such that, when implanted, it encompasses the nerve (SMP or splenic nerve) and the associated blood vessel (e.g., the SMP and associated mesenteric artery).

Each neuromodulation device 100 may carry out the required neuromodulation independently, or in response to one or more control signals. Such a control signal may be provided by the controller 104 according to an algorithm, in response to output of one or more detector elements 108, and/or in response to communications from one or more external sources received using the communications element. As discussed herein, the detector element(s) could be responsive to a variety of different physiological parameters.

FIG. 2B illustrates some ways in which the apparatus or system of FIG. 2A may be differently distributed. For example, in FIG. 2B the neuromodulation devices 100 comprise transducers 102 implanted proximally to a splenic nerve or SMP 90, but other elements such as a controller 104, a communication element 106 and a power supply 110 are implemented in a separate control unit 130 which may also be implanted in (as shown in 2B), or otherwise carried by the patient. The control unit 130 then controls the transducers in both of the neuromodulation devices via connections 132 which may for example comprise electrical wires and/or optical fibres for delivering signals and/or power to the transducers.

In the arrangement of FIG. 2B one or more detectors 108 are located separately from the control unit, although one or more such detectors could also or instead be located within the control unit 130 and/or in one or both of the neuromodulation devices 100. The detectors may be used to detect one or more physiological parameters of the patient, and the controller element or control unit then causes the transducers to apply the signal in response to the detected parameter(s), for example only when a detected physiological parameter meets or exceeds a predefined threshold value. Physiological parameters which could be detected for such purposes include sympathetic tone; gut tissue and/or circulating norepinephrine (NE) levels; gut tissue and/or circulating substance P levels; gut tissue and/or circulating levels of one or more inflammatory markers (for example, TNFα, IL-6, IL-1β, MCP-1, IL-17, C-reactive protein, calprotectin). Similarly, a detected physiological parameter could be an action potential or pattern of action potentials in a nerve of the patient, for example in the splenic nerve, the SMP or the vagus nerve. In this embodiment, the action potential or pattern of action potentials may be associated with colitis.

A variety of other ways in which the various functional elements could be located and grouped into the neuromodulation devices, a control unit 130 and elsewhere are of course possible. For example, one or more sensors of FIG. 2B could be used in the arrangement of FIG. 2A or 2C or other arrangements.

FIG. 2C illustrates some ways in which some functionality of the apparatus or system of FIG. 2A or 2B is provided not implanted in the patient. For example, in FIG. 2C an external power supply 140 is provided which can provide power to implanted elements of the apparatus or system in ways familiar to the skilled person, and an external controller 150 provides part or all of the functionality of the controller 104, and/or provides other aspects of control of the apparatus or system, and/or provides data readout from the apparatus or system, and/or provides a data input facility 152. The data input facility could be used by a patient or other operator in various ways, for example to input data relating to the status of the patient (e.g., if they are experiencing abdominal pain or discomfort, are undergoing a colitic episode).

Each neuromodulation device may be adapted to carry out the neuromodulation required using one or more physical modes of operation which typically involve applying a signal to the splenic nerve and/or the SMP, such a signal typically involving a transfer of energy to (or from) the nerve(s). As already discussed, such modes may comprise modulating the nerve or nerves using an electrical signal, an optical signal, an ultrasound or other mechanical signal, a thermal signal, a magnetic or electromagnetic signal, or some other use of energy to carry out the required modulation. Such signals may be non-destructive signals. Such modulation may comprise increasing, inhibiting, blocking or otherwise changing the pattern of neural activity in the nerve or nerves. To this end, the transducer 90 illustrated in FIG. 2A could be comprised of one or more electrodes, one or more photon sources, one or more ultrasound transducers, one more sources of heat, or one or more other types of transducer arranged to put the required neuromodulation into effect.

The neural modulation device or apparatus or system may be arranged to increase neural activity of the splenic nerve and/or SMP by using the transducer(s) to apply a voltage or current, for example an AC waveform. The device or apparatus or system may be arranged to use the transducer(s) to apply a low frequency AC waveform, for example an AC waveform having a frequency of 0.01 Hz-1 kHz, 0.01-500 Hz, 0.01-100 Hz, 0.01-20 Hz, preferably 0.5-20 Hz, 1-15 Hz, 5-10 Hz. In certain embodiments, the signal comprises an AC waveform having a frequency of 0.01 Hz, 0.05 Hz, 0.1 Hz, 0.5 Hz, 1 Hz, 2 Hz, 3 Hz, 4 Hz, 5 Hz, 6 Hz, 7 Hz, 8 Hz, 9 Hz or 10 Hz, such as 10 Hz.

In certain embodiments, the electrical signal has a current of 0.1-20 mA, 0.1-10 mA, 0.1-5 mA, 0.1-3 mA, 0.1-1 mA, 0.1-0.5 mA, 0.16 mA-0.6 mA, 0.2-0.4 mA. In certain embodiments the electrical signal has a current of at least 0.16 mA. In certain embodiments, the electrical signal has a current of 0.1 mA, 0.15 mA, 0.16 mA, 0.18 mA, 0.2 mA, 0.2 mA, 0.4 mA, 0.6 mA, 1 mA, 2 mA, 3 mA, 5 mA, 10 mA, for example 0.2 mA.

In certain embodiments, the electrical signal has a square waveform, a sinusoidal waveform, a saw-toothed waveform or a triangular waveform. In certain preferred embodiments, the signal has a square waveform.

In certain embodiments the electrical signal has a pulse width of 20-500 microseconds (μs). In certain embodiments the signal has a pulse width of 20-500 μs, 30-400 μs, 40-300 μs, 50-200 μs, 60-150 μs, 70-120 μs, 80-100 μs.

In certain embodiments, the electrical signal comprises a DC waveform and/or an AC waveform having a voltage of 0.1-20V. In certain preferred embodiments, the signal has a voltage of 0.1-15V, optionally 0.1-10V. In certain preferred embodiments the voltage is selected from 0.1V, 0.2V, 0.3V, 0.5V, 0.6V, 0.7V, 0.8V, 0.9V, 1V, 2V, 3V, 5V and 10V.

In certain embodiments, the electrical signal comprises an AC square biphasic waveform of 10 Hz 0.2 mA.

Neuromodulation techniques for stimulating neural activity include thermal, physical, chemical and electromagnetic techniques.

Temperature changes affect the ion channels in the membranes of neurons and produce complex changes in function, often affecting characteristics such as resting potential and rate of depolarization. Specifically, heating regions in the hypothalamus of cats has caused increased rates of spontaneous discharge (Teruo Nakayama, H. T. Hammel, J. D. Hardy, J. S. Eisenman American Journal of Physiology Published Jun. 1, 1963 Vol. 204 no. 1122-1126, incorporated herein by reference). Focused application of heat through short pulses of infrared (IR) radiation causes a transient local temperature increase and can also depolarize neurons (Loyal V, 2012 November; 295(11):1987-99, incorporated herein by reference). Advantages of IR radiation over electrical stimulation include higher spatial-temporal resolution and avoidance of electrical artifacts that can interfere with neural signal recoding. To further enhance laser stimulation, plasmonic gold nanorods injected near the membrane have been shown to transduce near IR energy into heat (Eom K, Small. Oct. 15, 2014; 10(19):3853-7 (incorporated herein by reference)). Magnetic fields have also been shown to heat nanoparticles to produce action potentials in neighbouring neurons (Heng Huang, Nature Nanotechnology 5, 602-606 (2010), incorporated herein by reference).

Mechanical deformation can also change membrane potential. Rapid, short duration mechanical compression of axons produces depolarization (Fred J. Julian And David E. Goldman, The Journal of General Physiology: Published Nov. 1, 1962, incorporated herein by reference). Also, applying a load to elongate an axon causes the axon to eventually depolarize. At elongations greater than 20%, the axon is irreversibly damaged (J. A. Galbraith, J Biomech Eng 115(1), 13-22 (Feb. 1, 1993), incorporated herein by reference). Ultrasound has been used for stimulating neural tissue structures including regions of the brain, retina and cochlear (King, R, Ultrasound Med. Biol. July 2014, Vol. 40 Issue 7, p1512, 11; Menz, M D, J Neurosci. Mar. 6, 2013; 33(10):4550-60; L. R. Gavrilov, Ultrasound Med Biol, 22 (1996), pp. 179-192, all of which are incorporated herein by reference). Studies using an in vitro hippocampal preparation suggested a simultaneous mechanical and thermal mechanism of modifying evoked field potentials (Bachtold, M. Ultrasound Med Biol. 1998 May; 24(4):557-65, incorporated herein by reference). The spatial resolution of ultrasound stimulation in the order of a few millimeters. The ultrasound pressure waves can penetrate deep within tissue, but are reflected at tissue interfaces with acoustic impedance mismatches.

Non-invasive magnetic stimulation has been used to stimulate the brain, spinal cord, nerve roots and peripheral nerves (Rossini, P M et al, Clin Neurophysiol. 2015 February, incorporated herein by reference). Quickly changing magnetic fields produces electrical currents that cause depolarization within the axons of neural tissue.

The techniques discussed above principally relate to the stimulation of neuronal activity. Where modulation by inhibiting or blocking activity or otherwise modifying activity in various ways is required, transducers may be configured to apply one or more of the blocking techniques described below.

Thermal methods of neuromodulation may also manipulate the temperature of a nerve to inhibit signal propagation. For example, Patberg et al. (Blocking of impulse conduction in peripheral nerves by local cooling as a routine in animal experimentation; Journal of Neuroscience Methods 1984; 10:267-75, which is incorporated herein by reference) discuss how cooling a nerve blocks signal conduction without an onset response, the block being both reversible and fast acting, with onsets of up to tens of seconds. Heating the nerve can also be used to block conduction, and is generally easier to implement in a small implantable or localised transducer or device, for example using infrared radiation from laser diode or a thermal heat source such as an electrically resistive element, which can be used to provide a fast, reversible, and spatially very localised heating effect (see for example Duke et al. J Neural Eng. 2012 June; 9(3):036003. Spatial and temporal variability in response to hybrid electro-optical stimulation, which is incorporated herein by reference). Either heating, or cooling, or both could be provided using a Peltier element.

Optogenetics is a technique that genetically modifies cells to express photosensitive features, which can then be activated with light to modulate cell function. Many different optogenetic tools have been developed that can be used to inhibit neural firing. A list of optogenetic tools to suppress neural activity has been compiled (Epilepsia. Oct. 9, 2014. doi: 10.1111/epi.12804. WONOEP appraisal: Optogenetic tools to suppress seizures and explore the mechanisms of epileptogenesis. Ritter L M et al., which is incorporated herein by reference). Acrylamine-azobenzene-quaternary ammonium (AAQ) is a photochromic ligand that blocks many types of K+ channels and in the cis configuration, the relief of K+ channel block inhibits firing (Nat Neurosci. 2013 July; 16(7):816-23. doi: 10.1038/nn.3424. Optogenetic pharmacology for control of native neuronal signaling proteins Kramer R H et al, which is incorporated herein by reference). By adapting Channelrhodopsin-2 and introducing it into mammalian neurons with the lentivirus, it is possible to control inhibitory synaptic transmission (Boyden E S 2005). Instead of using an external light source such as a laser or light emitting diode, light can be generated internally by introducing a gene based on firefly luciferase (Land B B 2014). The internally generated light has been sufficient to generate inhibition.

Mechanical forms of neuromodulation can include the use of ultrasound which may conveniently be implemented using external instead of implanted ultrasound transducers. Other forms of mechanical neuromodulation include the use of pressure (for example see "The effects of compression upon conduction in myelinated axons of the isolated frog sciatic nerve" by Robert Fern and P. J. Harrison Br.j. Anaesth. (1975), 47, 1123, incorporated herein by reference).

Some electrical forms of neuromodulation may use direct current (DC), or alternating current (AC) waveforms applied to a nerve using one or more electrodes. A DC block may be accomplished by gradually ramping up the DC waveform amplitude (Bhadra and Kilgore, IEEE Transactions on Neural systems and rehabilitation engineering, 2004 12(3) pp 313-324, which is incorporated herein by reference). Some AC techniques include HFAC or KHFAC (high-frequency or kilohertz frequency) to provide a reversible block (for example see Kilgore and Badra, 2004, Medical and Biological Engineering and Computing, the content of which is incorporated herein by reference for all purposes). In the work of Kilgore and Bhadra, a proposed waveform was sinusoidal or rectangular at 3-5 kHz, and typical signal amplitudes that produced block were 3-5 Volts or 0.5 to 2.0 milli Amperes peak to peak.

HFAC may typically be applied at a frequency of between 1 and 50 kHz at a duty cycle of 100% (Bhadra, N. et al., Journal of Computational Neuroscience, 2007, 22(3), pp 313-326, which is incorporated herein by reference). Methods for selectively blocking activity of a nerve by application of a waveform having a frequency of 5-10 kHz are described in U.S. Pat. No. 7,389,145 (incorporated herein by reference). Similarly, U.S. Pat. No. 8,731,676 (incorporated herein by reference) describes a method of ameliorating sensory nerve pain by applying a 5-50 kHz frequency waveform to a nerve.

The invention also provides a method of treating colitis in a patient, in particular IBD, the method comprising applying a signal to the splenic nerve and/or the superior mesenteric plexus (SMP) of the patient to modulate the neural activity of the nerve in the patient. In certain embodiments, a first signal is applied to the splenic nerve and a second signal is applied to the SMP.

In certain embodiments, the signal or signals are applied by a neuromodulation device comprising a transducer configured to apply each signal, preferably an electrode to apply an electrical signal. In certain preferred embodiments the neuromodulation device is at least partially implanted in the patient. In certain preferred embodiments, the neuromodulation device is wholly implanted in the patient.

In certain embodiments wherein a first signal is applied to the splenic nerve and a second signal is applied to the SMP, both signals are applied by the same neuromodulation device, that device have at least two transducers, one to apply the first signal and one to apply the second signal. In certain alternative embodiments, the first signal is applied by one neuromodulation device and the second signal is applied by a separate neuromodulation device.

In certain embodiments, the signal is configured to stimulate the nerve to which it is applied. In certain embodiments, the signal is configured to increase the neural activity in the nerve to which it is applied (an increase in the total signalling activity of the whole nerve, or in a subset of nerve fibres of the nerve, compared to baseline neural activity in that nerve or subset thereof).

In certain preferred embodiments, the method is a method of treating IBD. In certain such embodiments, the method is a method of treating ulcerative colitis or Crohn's Disease.

In certain embodiments, the treatment of colitis is prophylactic treatment. That is, the methods of the invention reduce the frequency of colitis episodes and/or prolong periods of remission.

In certain embodiments, the treatment of colitis is therapeutic treatment. That is, the methods of the invention at least partially relieve or ameliorate the severity of a colitic episode. For example, in certain embodiments the method provides amelioration of the frequency and/or severity of symptoms during an episode, or causes the patient to enter a state of remission. Therapeutic treatment may entirely cure the patient of colitis.

In certain embodiments, treatment of colitis is indicated by an improvement in a measurable physiological parameter, for example an increase in sympathetic tone, an increase in gut tissue and/or circulating nor-epinephrine, a decrease in one or more inflammatory markers (for example inflammatory cytokines (e.g., TNFalpha, IL-6, IL-1β, MCP-1, IL-17, C-reactive protein, calprotectin) in gut tissue and/or circulation, a decrease in gut pathology (for example as measured by endoscopy and/or histology, e.g., crypt loss, polyps, hyperplasia, goblet cell depletion), a decrease in colon fibrosis, and a reduction in symptom severity (such as a reduction of one or more of abdominal swelling, cramping, pain or discomfort, diarrhoea, weight loss, rectal bleeding, vomiting, anemia, elevated temperature and fatigue).

Suitable methods for determining the value for any given parameter would be appreciated by the skilled person.

In certain embodiments, treatment of the condition is indicated by an improvement in the profile of neural activity in the nerve or nerves to which a signal is applied. That is, treatment of the condition is indicated by the neural activity in the nerve(s) approaching the neural activity in a healthy individual—i.e., the pattern of action potentials in the nerve more closely resembling that exhibited by a healthy individual than before the intervention.

The following description and embodiments apply independently to each of those embodiments wherein a signal is applied to the splenic nerve, those embodiments wherein a signal is applied to the SMP, and those embodiments wherein a first signal is applied to the splenic nerve and a second signal is applied to the SMP. In those embodiments in which a first signal is applied to the splenic nerve and a second signal is applied to the SMP, the first and second signals are independently selected.

In certain embodiments, the modulation in neural activity as a result of applying a signal is an increase in neural activity in the nerve to which the signal is applied. That is, in such embodiments, application of the signal results in the neural activity in at least part of the nerve being increased compared to the baseline neural activity in that part of the nerve. Such an increase in activity could equally be achieved across the whole nerve. Therefore, in certain such embodiments, a result of applying the signal is an increase in neural activity across the whole nerve. Treatment of colitis is expected to be particularly effective when sympathetic signalling by the splenic nerve or the SMP, or both, is increased.

In certain embodiments, the signal or signals applied by the one or more transducers to increase neural activity is an electrical signal applied by an electrode, for example a voltage or current. In certain such embodiments the signal applied comprises a direct current (DC) waveform, such as a charge balanced direct current waveform, or an alternating current (AC) waveform, or both a DC and an AC waveform.

In certain embodiments, the electrical signal comprises a square waveform, a sinusoidal waveform, a saw-toothed waveform or a triangular waveform. In certain preferred embodiments, the signal has a square waveform.

In certain embodiments the electrical signal applied to increase neural activity comprises a low frequency AC waveform. In certain embodiments, the electrical signal is an AV waveform having a frequency of 0.01 Hz-1 kHz, 0.01-900 Hz, 0.01-800 Hz, 0.01-700 Hz, 0.01-600 Hz, 0.01-500 Hz, 0.01-400 Hz, 0.01-300 Hz, 0.01-200 Hz, 0.01-100 Hz, 0.01-50 Hz. In certain such embodiments the signal comprises an AC waveform having a frequency of 0.01-20 Hz, preferably 0.5-20 Hz, 1-15 Hz, 5-10 Hz. In certain embodiments, the signal comprises an AC waveform having a frequency of about 0.01 Hz, 0.05 Hz, 0.1 Hz, 0.5 Hz, 1 Hz, 2 Hz, 3 Hz, 4 Hz, 5 Hz, 6 Hz, 7 Hz, 8 Hz, 9 Hz or 10 Hz, for example 10 Hz.

In certain embodiments, the electrical signal has a current of 0.1-20 mA, 0.1-10 mA, 0.1-5 mA, 0.1-3 mA, 0.1-1 mA, 0.1-0.5 mA, 0.16 mA-0.6 mA, 0.2-0.4 mA. In certain embodiments the electrical signal has a current of at least 0.16 mA. In certain embodiments, the electrical signal has a current of 0.1 mA, 0.15 mA, 0.16 mA, 0.18 mA, 0.2 mA, 0.2 mA, 0.4 mA, 0.6 mA, 1 mA, 2 mA, 3 mA, 5 mA, 10 mA.

In certain embodiments the electrical signal has a pulse width of 20-500 microseconds (μs). In certain embodiments the signal has a pulse width of 20-500 μs, 30-400 μs, 40-300 μs, 50-200 μs, 60-150 μs, 70-120 μs, 80-100 μs.

In certain embodiments, the electrical signal comprises a DC waveform and/or an AC waveform having a voltage of 0.1-20V. In certain preferred embodiments, the signal has a voltage of 0.1-15V, optionally 0.1-10V. In certain preferred embodiments the voltage is selected from 0.1V, 0.2V, 0.3V, 0.5V, 0.6V, 0.7V, 0.8V, 0.9V, 1V, 2V, 3V, 5V and 10V.

In certain exemplary embodiments, the electrical signal comprises an AC square biphasic waveform of 10 Hz 0.2 mA.

In certain embodiments the modulation in neural activity as a result of applying a signal is inhibition of neural activity in the nerve to which the signal is applied (e.g., in a nerve other than the splenic nerve or SMP). That is, in such embodiments, application of the signal results in the neural activity in at least part of the nerve being reduced compared to the neural activity in that part of the nerve prior to the signal being applied. Therefore, in certain embodiments, a result of applying the signal is at least partial inhibition of neural activity in the nerve. In certain embodiments, a result of applying the signal is full inhibition of neural activity in the nerve or nerves.

In certain embodiments, the modulation in neural activity as a result of applying the signal is an alteration to the pattern of action potentials in nerve or nerves to which a signal is applied. In certain such embodiments, the neural activity is modulated such that the resultant pattern of action potentials in the nerve or nerves resembles the pattern of action potentials in the nerve(s) observed in a healthy subject.

In certain embodiments, the controller causes the signal to be applied intermittently. In certain such embodiments, the controller causes the signal to applied for a period of time (e.g., a first time period), then stopped for a second or immediately subsequent time period, then reapplied and stopped in an alternating pattern, e.g., applied for a third time period, then stopped for a fourth time period. In such an embodiment, the alternating periods of signal application and cessation (e.g., first, second, third and fourth periods, etc.) run sequentially and consecutively. The series of first, second, third and fourth periods (etc.) amounts to one application cycle. In certain such embodiments, multiple application cycles can run consecutively such that the signal is applied in phases, between which phases no signal is applied.

In such embodiments, the duration of the first, second, third and fourth time periods can be independently selected. That is, the duration of each time period may be the same or different to any of the other time periods. In certain such embodiments, the duration of each of the first, second, third and fourth time periods is any time from 5 seconds (5 s) to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h (or any combination of such lower and upper limits). In certain embodiments, the duration of each of the (e.g., first, second, third and fourth) time periods is 5 s, 10 s, 30 s, 60 s, 2 min, 5 min, 10 min, 15 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h (or any time period within the limits of a preceding time period).

In certain preferred embodiments, the alternating period of signal application (e.g., first and third time periods, etc.) is from 1 minute to 1 hour, such as 1-20 minutes, 1-10 minutes, 2-10 minutes, for example 2 minutes, or 5 minutes, or 10 minutes, or 20 minutes, or 30 minutes or an hour (or any period in between). In certain such embodiments, the alternating period of signal cessation (e.g., second and fourth time periods, etc.) are from 1-20 minutes, 1-10 minutes, 2-10 minutes, for example 2 minutes, or 5 minutes, or 10 minutes. In certain such embodiments, the signal is applied up to 6 times per day, up to 4 times per day, up to 3 times per day, 2 times per day, once per day. In certain such embodiments, the signal is not applied during alternating periods that are independently selected from 24 hours, 12 hours, 8 hours, and 6 hours (or selected to be of such duration from which the duration of the alternating period during which signal is applied, such that a diurnal repeating pattern is created and maintained). In certain such embodiments, the second and fourth periods comprise the remainder of a period of 24 hours, once the first and third periods, cumulatively, have been subtracted from 24 hours. That is, where the first and third period are, by way of example, 5 minutes each in duration (10 minutes total), the second and third periods comprise 23 hours and 40 minutes in total, that is 11 hours and 50 minutes each. Optionally in such embodiments, the first and second time periods, cumulatively, are a period of 12 hours, and the third and fourth time periods, cumulatively, are a period of 12 hours.

In certain embodiments wherein the controller causes the signal to be applied intermittently, the signal is applied for a specific amount of time per day, or a specific amount of time, twice a day. In certain such embodiments, the signal is applied for at least 2 min, at least 5 min, at least 10 min, at least 20 min, at least 30 min, at least 40 min, at least 50 min, at least 60 min, at least 90 min, at least 2 h, at least 3 h, at least 4 h, at least 5 h, at least 6 h, at least 7 h, at least 8 h, at least 9 h, at least 10 h, at least 11 h, at least 12 h, at least 13 h, at least 14 h, at least 15 h, at least 16 h, at least 17 h, at least 18 h, at least 19 h, at least 20 h, at least 21 h, at least 22 h, at least 23 h per day. In certain such embodiments, the signal is applied continuously for the specified amount of time. In certain alternative such embodiments, the signal may be applied discontinuously across the day, provided the total time of application amounts to the specified time. In a particular embodiment, the signal is applied for 2 min, 5 min, 10 min, 15 min, 20 min, 30 min, 45 min or 60 min, twice a day or four times a day.

In certain embodiments wherein the signal is applied intermittently, the signal is applied only when the patient is in a specific state. In certain such embodiments, the signal is applied only when the patient is experiencing an episode of colitis—i.e., the patient is experiencing one or more symptoms associated with a colitis crisis, such as abdominal pain or discomfort, diarrhoea, weight loss, rectal bleeding and fatigue. In such embodiments, the status of the patient (e.g., that they are experiencing an episode of colitis (a colitic episode) can be indicated by the patient. In certain embodiments in which the signal is applied by a neuromodulation device, the device may further comprise an input element enabling the patient to indicate their status. In alternative such embodiments, the status of the patient can be detected independently from any input from the patient. In certain embodiments in which the signal is applied by a neuromodulation device, the device may further comprise a detector configured to detect the status of the patient, wherein the signal is applied only when the detector detects that the patient is in the specific state.

In certain embodiments of methods according to the invention, the method further comprises the step of detecting one or more physiological parameters of the patient, wherein the signal is applied only when the detected physiological parameter meets or exceeds a predefined threshold value. In such embodiments wherein more than one physiological parameter is detected, the signal may be applied when any one of the detected parameters meets or exceeds its threshold value, alternatively only when all of the detected parameters meet or exceed their threshold values. In certain embodiments wherein the signal is applied by a neuromodulation device, the device further comprises at least one detector element configured to detect the one or more physiological parameters.

In certain embodiments, the one or more detected physiological parameters are selected from: sympathetic tone; gut tissue and/or plasma nor-epinephrine (NE) levels; gut tissue and/or circulating substance P levels; gut tissue and/or plasma levels of one or more inflammatory markers (for example, TNFα, IL-6, IL-1β, MCP-1, IL-17, C-reactive protein, calprotectin).

In certain embodiments, the one or more detected physiological parameters may include an action potential or pattern of action potentials in a nerve of the patient. In certain such embodiments the action potential or pattern of action potentials may be associated with colitis. In certain such embodiments, the nerve is the splenic nerve or SMP. In certain embodiments, the action potential or pattern of action potentials is detected in the vagus nerve, for example the afferent fibres of the vagus nerve.

It will be appreciated that any two or more of the indicated physiological parameters may be detected in parallel or consecutively. For example, in certain embodiments, the pattern of action potentials in the SMP can be detected at the same time as gut norepinephrine levels.

In certain embodiments, the signal is permanently applied. That is, once begun, the signal is continuously applied to the nerve.

It will be appreciated that if the signal is a series of pulses, gaps between pulses do not mean the signal is not continuously applied.

In certain embodiments of the methods, the modulation in neural activity caused by the application of a signal (whether that is an increase, inhibition, block or other modulation of neural activity) is temporary. That is, upon cessation of the signal, neural activity in the nerve returns substantially towards baseline neural activity within 1-60 seconds, or within 1-60 minutes, or within 1-24 hours, optionally 1-12 hours, optionally 1-6 hours, optionally 1-4 hours, optionally 1-2 hours. In certain such embodiments, the neural activity returns substantially fully to baseline neural activity. That is, the neural activity following cessation of the signal is substantially the same as the neural activity prior to the signal being applied—i.e., prior to modulation.

In certain alternative embodiments, the modulation in neural activity caused by the application of a signal is substantially persistent. That is, upon cessation of the signal, neural activity in the nerve remains substantially the same as when the signal was being applied—i.e., the neural activity during and following modulation is substantially the same.

In certain embodiments, the modulation in neural activity caused by the application of a signal is at least partially corrective, preferably substantially corrective. That is, upon cessation of the signal, neural activity in the nerve more closely resembles the pattern of action potentials observed in a healthy subject than prior to modulation, preferably substantially fully resembles the pattern of action potentials observed in a healthy subject. In such embodiments, the modulation caused by the signal can be any modulation as defined herein. For example, application of the signal may result in an increase in neural activity, and upon cessation of the signal, the pattern of action potentials in the nerve or nerves resembles the pattern of action potentials observed in a healthy subject. By way of further example, application of the signal may result in modulation such that the neural activity resembles the pattern of action potentials observed in a healthy subject, and upon cessation of the signal, the pattern of action potentials in the nerve resembles the pattern of action potentials observed in a healthy subject. It is hypothesised that such a corrective effect is the result of a positive feedback loop.

In certain such embodiments, once first applied, the signal may be applied intermittently or permanently, as described in the embodiments above.

In certain embodiments, the signal applied is a non-destructive signal.

In certain embodiments of the methods according to the invention, the signal applied is an electrical signal applied by a neuromodulation device comprised of one or more electrodes. In certain such embodiments the signal comprises a direct current (DC) waveform, such as a charge balanced DC waveform, or an alternating current (AC) waveform, or both a DC and an AC waveform.

In certain embodiments, the electrical signal comprises a square waveform, a sinusoidal waveform, a saw-toothed waveform or a triangular waveform. In certain preferred embodiments, the signal has a square waveform.

In certain embodiments the electrical signal comprises a low frequency AC waveform. In certain embodiments, the electrical signal is an AV waveform having a frequency of 0.01 Hz-1 kHz, 0.01-900 Hz, 0.01-800 Hz, 0.01-700 Hz, 0.01-600 Hz, 0.01-500 Hz, 0.01-400 Hz, 0.01-300 Hz, 0.01-200 Hz, 0.01-100 Hz, 0.01-50 Hz. In certain such embodiments the signal comprises an AC waveform having a frequency of 0.01-20 Hz, such as 0.5-20 Hz, 1-15 Hz, 5-10 Hz. In certain embodiments, the signal comprises an AC waveform having a frequency of 0.01 Hz, 0.05 Hz, 0.1 Hz, 0.5 Hz, 1 Hz, 2 Hz, 3 Hz, 4 Hz, 5 Hz, 6 Hz, 7 Hz, 8 Hz, 9 Hz or 10 Hz, for example 10 Hz.

In certain embodiments, the electrical signal has a current of 0.1-20 mA, 0.1-10 mA, 0.1-5 mA, 0.1-3 mA, 0.1-1 mA, 0.1-0.5 mA, 0.16 mA-0.6 mA, 0.2-0.4 mA. In certain embodiments the electrical signal has a current of at least 0.16 mA. In certain embodiments, the electrical signal has a current of 0.1 mA, 0.15 mA, 0.16 mA, 0.18 mA, 0.2 mA, 0.2 mA, 0.4 mA, 0.6 mA, 1 mA, 2 mA, 3 mA, 5 mA, 10 mA, for example 0.2 mA.

In certain embodiments the electrical signal has a pulse width of 20-500 microseconds (μs). In certain embodiments the signal has a pulse width of 20-500 μs, 30-400 μs, 40-300 μs, 50-200 μs, 60-150 μs, 70-120 μs, 80-100 μs.

In certain embodiments, the electrical signal comprises a DC waveform and/or an AC waveform having a voltage of 0.1-20V. In certain preferred embodiments, the signal has a voltage of 0.1-15V, optionally 0.1-10V. In certain preferred embodiments the voltage is selected from 0.1V, 0.2V, 0.3V, 0.5V, 0.6V, 0.7V, 0.8V, 0.9V, 1V, 2V, 3V, 5V and 10V.

In certain exemplary embodiments, the electrical signal comprises an AC square biphasic waveform of 10 Hz 0.2 mA.

In certain embodiments in which the signal applied is an electrical signal, the signal is applied by an electrode, such as a cuff electrode. In certain such embodiments, the cuff is configured to encompass the nerve to which the signal is applied and optionally the associated blood vessel. For example, in certain embodiments in which an electrical signal is applied to the SMP, the signal is applied by a cuff electrode configured to encompass the SMP and the superior mesenteric artery.

In certain alternative embodiments, the signal applied is an electromagnetic signal (optionally an optical signal), a mechanical (optionally ultrasonic) signal, a thermal signal, a magnetic signal or any other type of signal. In such embodiments, the signal is applied by a neuromodulation device comprising at least one transducer, the transducer may be comprised of one or more photon sources, one or more ultrasound transducers, one more sources of heat, or one or more other types of transducer arranged to put the respective signal into effect.

In certain embodiments wherein the signal is a thermal signal, the signal reduces the temperature of the nerve (i.e., cools the nerve). In certain alternative embodiments, the signal increases the temperature of the nerve (i.e., heats the nerve). In certain embodiments, the signal both heats and cools the nerve.

In certain embodiments wherein the signal is a mechanical signal, the signal is an ultrasonic signal. In certain alternative embodiments, the mechanical signal is a pressure signal.

It will be particularly advantageous to combine the apparatuses, systems and methods of the invention with an anti-inflammatory agent. Anti-inflammatory agents such as steroids (for example corticosteroids such as prednisolone and hydrocortisone), 5 amino-salicilates (5-ASAs) (e.g., mesalazine), immunosuppressants (for example methotrexate, azathioprine, and cyclosporine); and anti-tumour necrosis factor agent (anti-TNFs,) (such as infliximab and adalimumab), are already used as treatments for colitic conditions such as IBD. These agents when used alone are not always effective and are associated with undesirable side-effects, such as bone degeneration, psychiatric changes and infection. However, when used in conjunction with the methods and apparatuses or systems of the present invention, it is expected that the combination will result in improved treatment efficacy compared to one intervention alone, and/or will reduce the side-effects experienced by the patient, for example by reducing the dose of the anti-inflammatory agent that is required.

Therefore, in certain embodiments, the method further comprises administration of an anti-inflammatory agent to the patient. In certain embodiments, the anti-inflammatory agent is selected from a steroid, a 5-ASA, methotrexate, azathioprine, cyclosporine, and an anti-TNF agent. In certain preferred such embodiments, the anti-inflammatory agent and modulation of neural activity have coterminous effect—that is, an anti-inflammatory effect caused by each intervention is substantially simultaneous with an anti-inflammatory effect caused by the other intervention. In certain such embodiments, the effect may be synergistic.

Another aspect of the invention provides an anti-inflammatory agent for use in a method of treating colitis in a patient, wherein the method comprises: (i) applying a signal to the splenic nerve and/or the superior mesenteric plexus of the patient to modulate the neural activity in the nerve in the patient; and (ii) administering the anti-inflammatory agent to the patient.

In certain embodiments, the anti-inflammatory agent is selected from a steroid, a 5-ASA, methotrexate, azathioprine, cyclosporine, and an anti-TNF agent.

In certain preferred embodiments, the anti-inflammatory agent and modulation of neural activity have coterminous effect—that is, an anti-inflammatory effect caused by each intervention is substantially simultaneous with an anti-inflammatory effect caused by the other intervention. In certain such embodiments, the effect may be synergistic.

In certain embodiments, a first signal is applied to the splenic nerve and a second signal is applied to the SMP.

In certain embodiments, the signal or signals are applied by a neuromodulation device comprising a transducer configured to apply each signal. In certain preferred embodiments the neuromodulation device is at least partially implanted in the patient. In certain preferred embodiments, the neuromodulation device is wholly implanted in the patient.

In certain embodiments wherein a first signal is applied to the splenic nerve and a second signal is applied to the SMP, both signals are applied by the same neuromodulation device, that device have at least two transducers, one to apply the first signal and one to apply the second signal. In certain alternative embodiments, the first signal is applied by one neuromodulation device and the second signal is applied by a separate neuromodulation device.

In certain preferred embodiments, the signal or signals is/are stimulatory signals to increase neural activity in the nerve or nerves to which a signal is applied. In certain such embodiments the signal or signals are an electrical signal applied by a neuromodulation device comprising an electrode. In certain embodiments in which the signal applied is an electrical signal, the signal is applied by an electrode, such as a cuff electrode. In certain such embodiments, the cuff is configured to encompass the nerve to which the signal is applied and optionally the associated blood vessel. For example, in certain embodiments in which an electrical signal is applied to the SMP, the signal is applied by a cuff electrode configured to encompass the SMP and the superior mesenteric artery.

In certain preferred embodiments, the anti-inflammatory agent is for use in treating IBD. In certain such embodiments, the anti-inflammatory agent is for use in treating ulcerative colitis or Crohn's Disease.

In certain embodiments, the treatment of colitis is prophylactic treatment. That is, the methods of the invention reduce the frequency of colitis episodes and/or prolong periods of remission.

In certain embodiments, the treatment of colitis is therapeutic treatment. That is, the methods of the invention at least partially relieve or ameliorate the severity of a colitic episode. For example, in certain embodiments the method provides amelioration of the frequency and/or severity of symptoms during an episode, or causes the patient to enter a state of remission. Therapeutic treatment may entirely cure the patient of colitis.

In certain embodiments, treatment of colitis is indicated by an improvement in a measurable physiological parameter, for example an increase in sympathetic tone, an increase in gut tissue and/or circulating nor-epinephrine, a decrease in one or more inflammatory markers (for example inflammatory cytokines (e.g., TNFα, IL-6, IL-1β, IL-12p70, MCP-1, IL-17, IL-23, C-reactive protein, calprotectin) in gut tissue and/or circulation, a decrease in gut pathology (for example as measured by endoscopy and/or histology, e.g., crypt loss, polyps, hyperplasia, goblet cell depletion), a decrease in colon fibrosis, and a reduction in symptom severity (such as in abdominal swelling, cramping, pain or discomfort, diarrhoea, weight loss, rectal bleeding, vomiting, anemia, elevated temperature and fatigue).

Suitable methods for determining the value for any given parameter would be appreciated by the skilled person.

In certain embodiments, treatment of the condition is indicated by an improvement in the profile of neural activity in the nerve or nerves to which a signal is applied. That is, treatment of the condition is indicated by the neural activity in the nerve(s) approaching the neural activity in a healthy individual—i.e., the pattern of action potentials in the nerve more closely resembling that exhibited by a healthy individual than before the intervention.

In certain embodiments, the anti-inflammatory agent is for use in a method in which step (i) is performed before step (ii), in which step (ii) is performed before step (i), or in which step (i) and step (ii) are performed concurrently. In certain preferred embodiments, an anti-inflammatory effect of step (i) and an anti-inflammatory effect of step (ii) are substantially simultaneous. That is, in certain embodiments, the anti-inflammatory agent and neuromodulation exert their anti-inflammatory effect at substantially the same time.

The following description and embodiments apply independently to each of those embodiments wherein a signal is applied to the splenic nerve, those embodiments wherein a signal is applied to the SMP, and those embodiments wherein a first signal is applied to the splenic nerve and a second signal is applied to the SMP. In those embodiments in which a first signal is applied to the splenic nerve and a second signal is applied to the SMP, the first and second signals are independently selected.

In certain embodiments, the modulation in neural activity as a result of applying a signal is an increase in neural activity in the nerve to which the signal is applied. That is, in such embodiments, application of the signal results in the neural activity in at least part of the nerve being increased compared to the baseline neural activity in that part of the nerve. Such an increase in activity could equally be achieved across the whole nerve. Therefore, in certain such embodiments, a result of applying the signal is an increase in neural activity across the whole nerve. Treatment of colitis is expected to be particularly effective when signalling by the splenic nerve or the SMP, or both, is increased.

In certain embodiments, the signal applied to increase neural activity is an electrical signal comprising an AC waveform of low frequency. In certain embodiments the electrical signal comprises a low frequency AC waveform. In certain embodiments, the electrical signal is an AV waveform having a frequency of 0.01 Hz-1 kHz, 0.01-900 Hz, 0.01-800 Hz, 0.01-700 Hz, 0.01-600 Hz, 0.01-500 Hz, 0.01-400 Hz, 0.01-300 Hz, 0.01-200 Hz, 0.01-100 Hz, 0.01-50 Hz. In certain such embodiments the signal comprises an AC waveform having a frequency of 0.01-20 Hz, for example 0.5-20 Hz, 1-15 Hz, 5-10 Hz. In certain embodiments, the signal comprises an AC waveform having a frequency of 0.01 Hz, 0.05 Hz, 0.1 Hz, 0.5 Hz, 1 Hz, 2 Hz, 3 Hz, 4 Hz, 5 Hz, 6 Hz, 7 Hz, 8 Hz, 9 Hz or 1.0 Hz, such as 10 Hz.

In certain embodiments, the electrical signal comprises a square waveform, a sinusoidal waveform, a saw-toothed waveform or a triangular waveform. In certain preferred embodiments, the signal has a square waveform.

In certain embodiments, the electrical signal has a current of 0.1-20 mA, 0.1-10 mA, 0.1-5 mA, 0.1-3 mA, 0.1-1 mA, 0.1-0.5 mA, 0.16 mA-0.6 mA, 0.2-0.4 mA. In certain embodiments the electrical signal has a current of at least 0.16 mA. In certain embodiments, the electrical signal has a current of 0.1 mA, 0.15 mA, 0.16 mA, 0.18 mA, 0.2 mA, 0.2 mA, 0.4 mA, 0.6 mA, 1 mA, 2 mA, 3 mA, 5 mA, 10 mA.

In certain embodiments the electrical signal has a pulse width of 20-500 microseconds (μs). In certain embodiments the signal has a pulse width of 20-500 μs, 30-400 μs, 40-300 μs, 50-200 μs, 60-150 μs, 70-120 μs, 80-100 μs.

In certain embodiments, the electrical signal comprises a DC waveform and/or an AC waveform having a voltage of 0.1-20V. In certain preferred embodiments, the signal has a voltage of 0.1-15V, optionally 0.1-10V. In certain preferred embodiments the voltage is selected from 0.1V, 0.2V, 0.3V, 0.5V, 0.6V, 0.7V, 0.8V, 0.9V, 1V, 2V, 3V, 5V and 10V.

In certain exemplary embodiments, the electrical signal comprises an AC square biphasic waveform of 10 Hz 0.2 mA.

In certain embodiments the modulation in neural activity as a result of applying a signal is inhibition of neural activity in the nerve (such as a nerve other than the splenic nerve or SMP) to which the signal is applied. That is, in such embodiments, application of the signal results in the neural activity in at least part of the nerve being reduced compared to the neural activity in that part of the nerve prior to the signal being applied. Therefore, in certain embodiments, a result of applying the signal is at least partial inhibition of neural activity in the nerve. In certain embodiments, a result of applying the signal is full inhibition of neural activity in the nerve or nerves.

In certain embodiments, the modulation in neural activity as a result of applying the signal is an alteration to the pattern of action potentials in nerve or nerves to which a signal is applied. In certain such embodiments, the neural activity is modulated such that the resultant pattern of action potentials in the nerve or nerves resembles the pattern of action potentials in the nerve(s) observed in a healthy subject.

In certain embodiments, the controller causes the signal to be applied intermittently. In certain such embodiments, the controller causes the signal to applied for a period of time (e.g., a first time period), then stopped for a second or immediately subsequent time period, then reapplied and stopped in an alternating pattern, e.g., applied for a third time period, then stopped for a fourth time period. In such an embodiment, the alternating periods of signal application and cessation (e.g., first, second, third and fourth periods, etc.) run sequentially and consecutively. The series of first, second, third and fourth periods (etc.) amounts to one application cycle. In certain such embodiments, multiple application cycles can run consecutively such that the signal is applied in phases, between which phases no signal is applied.

In such embodiments, the duration of the first, second, third and fourth time periods can be independently selected. That is, the duration of each time period may be the same or different to any of the other time periods. In certain such embodiments, the duration of each of the first, second, third and fourth time periods is any time from 5 seconds (5 s) to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h (or any combination of such lower and upper limits). In certain embodiments, the duration of each of the (e.g., first, second, third and fourth) time periods is 5 s, 10 s, 30 s, 60 s, 2 min, 5 min, 10 min, 15 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h (or any time period within the limits of a preceding time period).

In certain preferred embodiments, the alternating period of signal application (e.g., first and third time periods, etc.) is from 1 minute to 1 hour, such as 1-20 minutes, 1-10 minutes, 2-10 minutes, for example 2 minutes, or 5 minutes, or 10 minutes, or 20 minutes, or 30 minutes or an hour (or any period in between). In certain such embodiments, the alternating period of signal cessation (e.g., second and fourth time periods, etc.) are from 1-20 minutes, 1-10 minutes, 2-10 minutes, for example 2 minutes, or 5 minutes, or 10 minutes. In certain such embodiments, the signal is applied up to 6 times per day, up to 4 times per day, up to 3 times per day, 2 times per day, once per day. In certain such embodiments, the signal is not applied during alternating periods that are independently selected from 24 hours, 12 hours, 8 hours, and 6 hours (or selected to be of such duration from which the duration of the alternating period during which signal is applied, such that a diurnal repeating pattern is created and maintained). In certain such embodiments, the second and fourth periods comprise the remainder of a period of 24 hours, once the first and third periods, cumulatively, have been subtracted from 24 hours. That is, where the first and third period are, by way of example, 5 minutes each in duration (10 minutes total), the second and third periods comprise 23 hours and 40 minutes in total, that is 11 hours and 50 minutes each. Optionally in such embodiments, the first and second time periods, cumulatively, are a period of 12 hours, and the third and fourth time periods, cumulatively, are a period of 12 hours.

In certain embodiments wherein the controller causes the signal to be applied intermittently, the signal is applied for a specific amount of time per day, or a specific amount of time, twice a day. In certain such embodiments, the signal is applied for at least 2 min, at least 5 min, at least 10 min, at least 20 min, at least 30 min, at least 40 min, at least 50 min, at least 60 min, at least 90 min, at least 2 h, at least 3 h, at least 4 h, at least 5 h, at least 6 h, at least 7 h, at least 8 h, at least 9 h, at least 10 h, at least 11 h, at least 12 h, at least 13 h, at least 14 h, at least 15 h, at least 16 h, at least 17 h, at least 18 h, at least 19 h, at least 20 h, at least 21 h, at least 22 h, at least 23 h per day. In certain such embodiments, the signal is applied continuously for the specified amount of time. In certain alternative such embodiments, the signal may be applied discontinuously across the day, provided the total time of application amounts to the specified time. In a particular embodiment, the signal is applied for 2 min, 5 min, 10 min, 15 min, 20 min, 30 min, 45 min or 60 min, twice a day or four times a day.

In certain embodiments wherein the signal is applied intermittently, the signal is applied only when the patient is in a specific state. In certain such embodiments, the signal is applied only when the patient is experiencing an episode of colitis (alternatively, a colitic episode)—e.g., they are experiencing one or more symptoms associated with a colitis crisis or flare-up, such as abdominal swelling, cramping, pain or discomfort, diarrhoea, weight loss, rectal bleeding, vomiting, anemia, elevated temperature and fatigue. In such embodiments, the status of the patient (e.g., that they are experiencing an episode of colitis) can be indicated by the patient. In certain embodiments in which the signal is applied by a neuromodulation device, the device may further comprise an input element enabling the patient to indicate their status. In alternative such embodiments, the status of the patient can be detected independently from any input from the patient. In certain embodiments in which the signal is applied by a neuromodulation device, the device may further comprise a detector configured to detect the status of the patient, wherein the signal is applied only when the detector detects that the patient is in the specific state (e.g., in a colitic episode or flare-up).

In certain embodiments of methods according to the invention, the method further comprises the step of detecting one or more physiological parameters of the patient, and optionally applying the signal only when the detected physiological parameter meets or exceeds a predefined threshold value. In such embodiments wherein more than one physiological parameter is detected, the signal may be applied when any one of the detected parameters meets or exceeds its threshold value, alternatively only when all of the detected parameters meet or exceed their threshold values. In certain embodiments wherein the signal is applied by a neuromodulation device, the device further comprises at least one detector element configured to detect the one or more physiological parameters.

In certain embodiments, the one or more detected physiological parameters are selected from: sympathetic tone; gut tissue and/or circulating nor-epinephrine (NE) levels; gut tissue and/or circulating substance P levels; gut tissue and/or circulating levels of one or more inflammatory markers (for example, TNFα, IL-6, IL-1β, MCP-1, IL-17, C-reactive protein, calprotectin), blood flow and/or circulation through the colon and/or spleen.

In certain embodiments, the one or more detected physiological parameters may include an action potential or pattern of action potentials in a nerve of the patient. In certain such embodiments, the action potential or pattern of action potentials may be associated with colitis. In certain such embodiments, the nerve is the splenic nerve or SMP. In certain embodiments, the action potential or pattern of action potentials is detected in the vagus nerve, for example the afferent fibres of the vagus nerve.

It will be appreciated that any two or more of the indicated physiological parameters may be detected in parallel or consecutively. For example, in certain embodiments, the pattern of action potentials in the SMP can be detected at the same time as gut tissue NE levels.

In certain embodiments, the signal is permanently applied. That is, once begun, the signal is continuously applied to the nerve. It will be appreciated that in embodiments wherein the signal is a series of pulses, gaps between pulses do not mean the signal is not continuously applied.

In certain embodiments of the methods, the modulation in neural activity caused by the application of a signal (whether that is an increase, inhibition, block or other modulation of neural activity) is temporary. That is, upon cessation of the signal, neural activity in the nerve returns substantially towards baseline neural activity within 1-60 seconds, or within 1-60 minutes, or within 1-24 hours, optionally 1-12 hours, optionally 1-6 hours, optionally 1-4 hours, optionally 1-2 hours. In certain such embodiments, the neural activity returns substantially fully to baseline neural activity. That is, the neural activity following cessation of the signal is substantially the same as the neural activity prior to the signal being applied—i.e., prior to modulation.

In certain alternative embodiments, the modulation in neural activity caused by the application of a signal is substantially persistent. That is, upon cessation of the signal, neural activity in the nerve remains substantially the same as when the signal was being applied i.e., the neural activity during and following modulation is substantially the same.

In certain embodiments, the modulation in neural activity caused by the application of a signal is at least partially corrective, preferably substantially corrective. That is, upon application (and optionally cessation) of the signal, neural activity in the nerve more closely resembles the pattern of action potentials observed in a healthy subject than prior to modulation, preferably substantially fully resembles the pattern of action potentials observed in a healthy subject. In such embodiments, the modulation caused by the signal can be any modulation as defined herein. For example, application of the signal may result in an increase in neural activity, and upon cessation of the signal, the pattern of action potentials in the nerve or nerves resembles the pattern of action potentials observed in a healthy subject. By way of further example, application of the signal may result in modulation such that the neural activity resembles the pattern of action potentials observed in a healthy subject, and upon cessation of the signal, the pattern of action potentials in the nerve resembles the pattern of action potentials observed in a healthy subject. It is hypothesised that such a corrective effect is the result of a positive feedback loop.

In certain such embodiments, once first applied, the signal may be applied intermittently or permanently, as described in the embodiments above.

In certain embodiments, the signal applied is a non-destructive signal.

In certain embodiments of the methods according to the invention, the signal applied is an electrical signal applied by a neuromodulation device comprised of one or more electrodes. In certain such embodiments the signal comprises a direct current (DC) waveform, such as a charge balanced DC waveform, or an alternating current (AC) waveform, or both a DC and an AC waveform.

In certain embodiments, the electrical signal comprises a square waveform, a sinusoidal waveform, a saw-toothed waveform or a triangular waveform. In certain preferred embodiments, the signal has a square waveform.

In certain embodiments the electrical signal comprises a low frequency AC waveform. In certain embodiments, the electrical signal is an AV waveform having a frequency of 0.01 Hz-1 kHz, 0.01-900 Hz, 0.01-800 Hz, 0.01-700 Hz, 0.01-600 Hz, 0.01-500 Hz, 0.01-400 Hz, 0.01-300 Hz, 0.01-200 Hz, 0.01-100 Hz, 0.01-50 Hz.

In certain such embodiments the signal comprises an AC waveform having a frequency of 0.01-20 Hz, preferably 0.5-20 Hz, 1-15 Hz, or 5-10 Hz, In certain embodiments, the signal comprises an AC waveform having a frequency of 0.01 Hz, 0.05 Hz, 0.1 Hz, 0.5 Hz, 1 Hz, 2 Hz, 3 Hz, 4 Hz, 5 Hz, 6 Hz, 7 Hz, 8 Hz, 9 Hz or 10 Hz, such as 10 Hz.

In certain embodiments, the electrical signal has a current of 0.1-20 mA, 0.1-10 mA, 0.1-5 mA, 0.1-3 mA, 0.1-1 mA, 0.1-0.5 mA, 0.16 mA-0.6 mA, 0.2-0.4 mA. In certain embodiments the electrical signal has a current of at least 0.16 mA. In certain embodiments, the electrical signal has a current of 0.1 mA, 0.15 mA, 0.16 mA, 0.18 mA, 0.2 mA, 0.2 mA, 0.4 mA, 0.6 mA, 1 mA, 2 mA, 3 mA, mA, 10 mA.

In certain embodiments the electrical signal has a pulse width of 20-500 microseconds ($\mu$s). In certain embodiments the signal has a pulse width of 20-500 $\mu$s, 30-400 $\mu$s, 40-300 $\mu$s, 50-200 $\mu$s, 60-150 $\mu$s, 70-120 $\mu$s, 80-100 $\mu$s.

In certain embodiments, the electrical signal comprises a DC waveform and/or an AC waveform having a voltage of 0.1-20V. In certain preferred embodiments, the signal has a voltage of 0.1-15V, optionally 0.1-10V. In certain preferred embodiments the voltage is selected from 0.1V, 0.2V, 0.3V, 0.5V, 0.6V, 0.7V, 0.8V, 0.9V, 1V, 2V, 3V, 5V and 10V.

In certain exemplary embodiments, the electrical signal comprises an AC square biphasic waveform of 10 Hz 0.2 mA.

In certain alternative embodiments, the signal applied is an electromagnetic signal (optionally an optical signal), a mechanical (optionally ultrasonic) signal, a thermal signal, a magnetic signal or any other type of signal. In such embodiments, the signal is applied by a neuromodulation device comprising at least one transducer, the transducer may be comprised of one or more photon sources, one or more ultrasound transducers, one more sources of heat, or one or more other types of transducer arranged to put the respective signal into effect.

In certain embodiments wherein the signal is a thermal signal, the signal reduces the temperature of the nerve (i.e., cools the nerve). In certain alternative embodiments, the signal increases the temperature of the nerve (i.e., heats the nerve). In certain embodiments, the signal both heats and cools the nerve.

In certain embodiments wherein the signal is a mechanical signal, the signal is an ultrasonic signal. In certain alternative embodiments, the mechanical signal is a pressure signal.

In another aspect, the invention provides a neuromodulatory electrical waveform for use in treating colitis, for example IBD, in a patient, wherein the waveform is an alternating current (AC) waveform having a frequency 0.01-20 Hz, such that, when applied to a splenic nerve and/or SMP of the patient, the waveform increases neural signalling in the nerve. In certain embodiments, the waveform, when applied to the nerve, relieves or prevents colitis.

In another aspect, the invention provides use of a neuromodulation device for treating colitis, for example IBD, in a patient by modulating neural activity in the splenic nerve and/or SMP of the patient.

In a preferred embodiment of all aspects of the invention, the subject or patient is a mammal, more preferably a human.

In a preferred embodiment of all aspects of the invention, the signal or signals is/are applied substantially exclusively to the nerves or nerve fibres specified, and not to other nerves (e.g., a vagus nerve) or nerve fibres.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

EXAMPLES

Example 1

Effects of Denervation in Animal Models of Colitis

Surgical sympathetic denervation (sympathectomy) of the colon and vagal denervation plus sympathetic denervation of the colon was performed as follows.

Mice

Standard eight to 12 week old C57/Bl6 pathogen free mice (weight range of 18-20 grams) were obtained from Charles River Laboratories (Maastricht, The Netherlands) and co-housed in the specified pathogen free animal facility at the Academic Medical Centre (Amsterdam, The Netherlands). Animals were housed under standard IVC conditions with a 12/12 light/dark cycle under constant conditions of temperature (20+/−2° C.) and humidity (55%) and ad libitum food and water. All experiments were performed under fentanyl-fluanisone (Hypnorm; Janssen, Beerse, Belgium)-midazolam (Hypnorm; Janssen, Beerse, Belgium) (FFM). All experiments were performed in accordance with the guidelines of the Laboratory Animal Use of the Netherlands and approved by the Ethical Animal Research Committee of the Academic Medical Center of Amsterdam. *Induction of DSS Colitis*

Use was made of a short term and longer term dextran sulfate sodium (DSS) colitis model as previously described (Melgar, Karlsson, & Michaelsson 2005, incorporated herein by reference). Mice were given 2% DSS in drinking water ad libitum which was changed on a daily basis. The duration of the experiments of acute and chronic colitis was 35 days altogether. Control animals included in the experiments were given normal drinking water. To induce an initial inflammatory state in the colon use was made of the short term (acute) colitis model mice were given DSS for the last 7 days of the experiment prior to euthanasia. To induce an initial inflammatory state followed by a recovery state to allow for the recovery of epithelial lesions, use was made of the longer term (chronic) colitis model. In this model, mice were given DSS for the first 5-7 days of the experiment after which they received normal drinking water for an additional 30 day period. To assess the severity of the induced colitis at termination colons were measured and mice were assigned an inflammatory and diarrhea score (as defined by Melgar et al. (Meigar, Karlsson, & Michaelsson 2005, incorporated herein by reference).

Anaesthesia

All surgical procedures were performed on anesthetized mice by injecting intraperitoneally (i.p.) a mixture of fentanylcitrate/fluanisone (Hypnorm; Janssen, Beerse, Belgium) and midazolam (Dormicum; Roche, Mijdrecht, The Netherlands). Postoperatively fynadine was injected subcutaneously. Before the dextran sodium sulphate (DSS) colitis experiment, mice had a recovery period of approximately 7 days.

Denervation Procedure

Mice were operated at 10-12 weeks of age after two week of adaptation in the animalacilities. Mice were anesthetized by an intraperitoneal (i.p.) injection of a mixture of fentanylcitrate/fluanisone (Hypnorm; Janssen, Beerse, Belgium) and midozolam (Dormicum; Roche, Mijdrecht, The Netherlands). Selective denervation of the vagal innervation of the colon was performed by cutting the right celiac branch of the vagus nerve, as described in Cailotto et al. (Cailotto, Costes, van, V, van Bree, van Heerikhuize, Buijs, & Boeckxstaens Neurogastro and Mot, 2012, incorporated herein by reference).

Vagal Denervation (Vagotomy) Validation

To validate the selectivity of the vagal surgical denervation of the small intestine, we used neuronal tracer technique. In brief, we injected retrograde neuronal tracer within the small bowel. After a period of 7 days, the retrograde tracer labeled the cell bodies of the vagal motor neurons (located in the DMV) and the sympathetic motor neurons in the mesenteric ganglion.

Performing a surgical cut of the vagal branch supplying the small bowel prior to retrograde tracer injection led to an absence of labeled cell bodies in the DMV (impossibility of the tracer to reach the DMV caused by 'cut-vagal' fibers). In contrast, we found the presence of sympathetic labeled cell bodies in the mesenteric ganglion, demonstrating that sympathetic fibers are still intact after vagal denervation.

A similar technical strategy was used to confirm that vagal denervation was affecting solely the proximal part of the colon and not the distal part. Injection of the tracer in the proximal colon leads to labeling vagal motor neurons in the DMV. In contrast, injection in the distal colon did not label motor neurons in the DMV, confirming that vagus nerve innervates only the proximal colon.

Surgical vagal denervation prior to retrograde tracer leads to the absence of labeled motor vagal neurons in the DMV. Of note, the presence of labeled sympathetic motor neurons in the mesenteric ganglion is still observed after vagal denervation showing that vagal denervation did not affect sympathetic innervation of the proximal colon.

Sympathetic Denervation of the Colon (i.e., Sympathectomy)

Sympathetic denervation was accomplished by transecting/dissecting the nerve tissue free from the superior mesenteric plexus that is located along the mesenteric artery. Cottons swaps were used to gently push the small intestine and expose the celiac and superior mesenteric arteries arising from abdominal aorta. The mesenteric artery was careful separated from the two lymph ducts that flank both side of the blood vessel. With thick forceps, the nerve bundle lying underneath the artery is isolated from the blood vessel and cut and/or dissected free from the artery.

The completeness of the denervation was confirmed by measuring the norepinephrine (NE) content in the small intestine (i.e., jejunum and ileum), proximal and distal part of the colon. Surgical ablation of the nerve bundle lead to a depletion of the NE content in the small intestine and proximal colon only, down to 10-15% of the original concentration. The efficiency of the surgical procedure was confirmed in all mice included in the described experiments by measuring the NE content in the small intestine. The sympathectomy was considered successful when the NE content was less than 15% of the NE content measurement in non-denervated intestine, according to (Colle, Van, Troisi, & De 2004, incorporated herein by reference).

Sympathetic Denervation of the Spleen

Splenic denervation was achieved by cutting noradrenergic fibers running along blood vessels supplying the spleen (splenic artery, lineal artery) and by cutting/dissecting free nerve fibers present in the conjunctive tissue located at each tip of the spleen as previously described (Cailotto et al., (2012) and Costes et al., (2014), each of which are incorporated herein by reference).

Completion of the denervation was assessed by Tyrosine Hydroxylase staining in intestinal and splenic tissue.

Electrode Implantation

The cuff electrode was implanted in the rat to be treated as follows: The skin of the abdomen was opened with scissors midline and skin was detached from the muscle. The connector wire is tunneled right laterally of the midline using scissor and steel rod in direction to the neck. The wire is approached via the right side of the animal. The wound is covered with moist (0.9% NaCl) gauze and the rat is turned over. A scalpel was used to make an incision on the head skin from between the eyes until between the ears over the skull. The tunnel allowing the wiring was placed from this side via the neck and the right side of the animal using the scissor and steel rod.

The animal was placed on its left side and the tunnel using the steel rod from the abdominal side (or which way the operator prefers) was completed. Next the tip of the stripet was slid over the steel rod on the neck side and tunneled through. Using some 0.9% NaCl, the cuff was tunneled through the stripet and tunneled underneath the skin. The abdomen was covered with wetted (0.9% NaCl) gauze and the rat was turned back on the abdominal side. The prepared pedestal was now employed and marked with a marker to mark the 4 drill points. Four holes were drilled (using 0.9% 1.0 NaCl as coolant) in the skull (drill bit 9 was used) and 4 screws were placed with the screwdriver (two whole rounds upon first "grip").

Next the pedestal was glued (Roti) and placed on the skull (skull was dried and cleaned in advance). The powder and fluid from the two component dental cement in the mix palette was combined and crafted with the spatula an oval form covering the screws and the pedestal. It was made sure that the outside was smooth and round. Afterwards, the head wound was cleaned to remove access chemicals. The wound was stitched with one stitch before and one or two behind the pedestal. The aluminum cap was placed on top of the pedestal. Supports were generated from gauze pads and the rat was turned on its back, supporting the head mount.

Next, the abdominal cavity was opened over the linea alba and wetted cotton swabs were applied to carefully takeout the intestine to make room for exploring the mesenteric artery, putting the intestine on the side (on and under wetted gauze). The mesenteric artery was carefully cleaned using forceps, without destroying the lymph ducts. A sharp scissor was applied next to puncture the abdominal wall to tunnel through the cuff electrode (using forceps). The cuff was placed around the SMP and artery. Cuff flaps were closed with one silk 6.0 suture. The intestinal mass was placed back in the abdominal cavity and the abdominal muscle was closed with continuous suture (Vycril 3.0). The skin was closed with U shaped sutures. The rat was placed back in its cage to recover. Proper aftercare, e.g., painkilling and baytril 24 hours after surgery etc, were provided, during continuous monitoring of the recovery period.

Sacrifice and Sample Collection

Animals were sacrificed at day 7 or day 12 after the first day of DSS exposure. Animals were anesthetized with pentobarbital (0.1 mL of a 50 mg/mL solution). Mice were sacrificed by transcardiac perfusion with phosphate buffered saline (PBS) followed by 4% paraformaldehyde (PFA; pH 7.4). Colonic tissue was collected prior to PFA perfusion. Colon length, inflammatory score (i.e., severity of fibrosis) and diarrhea score were assessed as previously described (Melgar et al., 2005) by a blinded observer. Entire colons were then snap-frozen for PCR analysis. Brains were collected after PFA perfusion, postfixed overnight (4° C.) and cryo-protected by immersion with 30% sucrose in 0.2 mol·L-1 PBS (pH 7.4) at 4° C. overnight and kept at 4° C. until analysis.

RNA Isolation, cDNA Synthesis and QPCR

Total mRNAs from entire colon were extracted after homogenization of the samples in TriPure isolation reagent according to the manufacturer's instructions (Roche Applied Science). cDNA synthesis was performed using the Revertaid first strand cDNA synthesis kit (Fermentas) and Real-time PCR was performed using a SYBR green master mix (Roche Applied Science) on a Lightcycler 480 (Roche Applied Science). The primers used (synthesized by Invitrogen, Bleiswijk, The Netherlands) are described in Table 1. Analysis was performed using the LinRegPCR program (AMC, Amsterdam, The Netherlands) (Ruijter et al., 2009). The target gene expression was normalized over the expression of 2 reference genes selected after analysis with the Genorm software. All data are expressed in AU and represent relative expression over the control group.

Statistical Analysis

Statistical analysis was performed using the SPSS 19.0 software (SPSS Inc, Chicago, Ill.). Data are expressed as mean±SEM. Normal distribution was assessed using the Kolmogorov-Smirnov test. Square-root normalization was applied to non-normal data sets. Whenever two groups of data were compared (i.e., Ctrl vs DSS), a Student t-test was performed. Whenever the influence of 2 independent variables (i.e., Ctrl/DSS and denervation) was analyzed, a two-way ANOVA was performed to determine the interaction between denervation (Sham vs Vx/Sx) and treatment (Ctrl vs DSS). When significance was observed (i.e., $p<0.05$) an unpaired Student t-test was performed to evaluate the significance between Sham vs Vx/Sx or Ctrl vs DSS.

Rats

Hsd:Sprague Dawley rats were purchased from Envigo (Horst, The Netherlands) and co-housed in a specified pathogen free facility with a 12/12 light/dark cycle under constant conditions of temperature (20±2° C.) and humidity (55%) and ad libitum food and water. All experiments were performed under 3% isoflurane/$O_2$ anaesthesia and all efforts were made to minimize the suffering of the animals. All experiments were performed in accordance with the guidelines of the Laboratory Animal Use of the Netherlands and approved by the Ethical Animal Research Committee of the Academic Medical Centre of Amsterdam.

Implantation of the Cuff Electrode Around the Superior Mesenteric Nerve

The rat was anesthetized with 3% isoflurane/$O_2$ and pre-operatively Metacam 1 mg/kg (Boehringer, Ingelheim am Rein, Germany) and Baytril 10 mg/kg (Bayer Healthcare, Whippany, N.J., USA) were given subcutaneously. 1) The skin of the abdomen was opened and detached from the muscle. With a scalpel, an incision was made on the head between the eyes until between the ears and the skull cleaned. A tunnel was made with a steel rod subcutaneously from the side of the neck via the back towards the incision made in the skin of the abdomen via the right flank of the animal. The electrode (500 μm tunnelcuff tripolar; CorTec GmbH, Freiburg, Germany) was placed subcutaneously through the tunnel. 2) With a drill, 4 holes were drilled in the skull and 4 screws were placed with a screwdriver. The pedestal (PlasticsOne, Phoenix, Ariz., USA; Cat No MS303-120) that connects the wires of the electrode to the generator was placed on the skull between the screws and attached firmly to the skull and the screws with dental cement and the skin around is closed with 2 sutures. 3) The abdominal cavity was opened and the mesenteric artery (along which the nerve fibres are positioned) was located. A whole was made in the abdominal wall and the electrode was tunnelled through. The electrode was placed around the superior mesenteric artery and fixated with one suture in the flaps of the electrode. After placement, the abdominal wall and skin was closed. 24 hours post-operatively Metacam 1 mg/kg and Baytril 10 mg/kg was given subcutaneously.

Acute DSS-Induced Colitis in Rats

Two weeks after the operation, rats were given 5% (w/v) DSS (TdB Consultancy, Uppsala, Sweden) ad libitum in drinking water for 9 consecutive days. The DSS solution was replaced daily. Consistence of the stool, anal bleedings, general behaviour and posture, and weight were assessed daily. Animals were sacrificed at day 9 after the first day of DSS exposure.

Superior mesenteric nerve stimulation: 3 days after the start of DSS, electric stimulation was given twice a day for 5 minutes, 10 Hz, 1 ms and 200 μA till the day of sacrifice. The control rats were also connected to the generated but no electrical pulse was given.

Endoscopy

For endoscopy, rats were anesthetized with 3% isoflurane/$O_2$ and stool was removed as much as possible. The Olympus URF type V endoscope was rectally inserted for a maximum of 10 centimetres and videos of the endoscopy were recorded using a Medicap USB200 Medical Digital Video Recorder, when retracting the endoscope. The endoscopy movies were scored according to the murine endoscopic index of colitis severity (MEICS; Table 1), by a blinded observer from 0-15 as reported.

TABLE 1

| | Endoscopy score | | | |
|---|---|---|---|---|
| | Score | | | |
| | 0 | 1 | 2 | 3 |
| Stool | Normal/solid | Still shaped | Unshaped | Spread |
| Thickening | Transparent | Moderate | Marked | Intransparent |
| Vascularity | Normal | Moderate | Marked | Bleeding |
| Fibrin | None | Little | Marked | Extreme |
| Granularity | None | Moderate | Marked | Extreme |

Sample Collection

After endoscopy, the animals were sacrificed using 100% $CO_2$ and blood was obtained by cardiac puncture and stored as serum. Wet weights of spleen and colon were recorded together with the total length of the colon. Colon weight per cm was used as a disease parameter. Stool was scored as follows: 0) normal faeces, 1) soft pellets, 2) thin faeces, 3) watery diarrhoea, 4) bloody diarrhoea. Spleen, duodenum, jejunum, ileum and colon were collected for RNA and protein isolation and snap frozen. The most proximal and distal part of the colon were used for histological assessment.

Histological Assessment

The longitudinally opened colons were rolled, fixed in 4% formalin and embedded in paraffin for routine histology. An experienced pathologist evaluated formalin-fixed haematoxylin tissue sections microscopically, in a blinded fashion. Colons were evaluated based on six characteristics of inflammation explained in Table 2. The sum pathology score was calculated as the sum of the characteristics scored.

TABLE 2

| Pathology score used for histological evaluation by pathologist. | | | | | |
|---|---|---|---|---|---|
| | Score | | | | |
| | 0 | 1 | 2 | 3 | 4 |
| Mono- and polymorphonuclear infiltrate | Normal | Increase in mucosa | Increase in mucosa and submucosa | Extending into mucosa, submucosa, tunica muscularis and/or serosa | |
| Goblet cells | Normal, large amount | Depletion of <10% | Depletion of 10-50% | Depletion of >50% | |
| Crypt loss | No crypt loss | <10% crypt loss | 10-50% crypt loss | >50% crypt loss | |
| Epithelial hyperplasia | Normal | Slight hyperplasia | 2-3x increase of crypt length | >3x increase of crypt length | |
| Ulcerations | No ulceration | | | | Ulcerations |
| Crypt abscesses | No abscesses | | | | Crypt abscesses |

RNA Isolation, cDNA Synthesis and Quantitative Polymerase Chain Reaction (qPCR)

Total mRNAs from colonic tissue were extracted after homogenization of the samples in TriPure isolation reagent according to the manufacturer's instructions (Roche Applied Science, Basel, Switzerland). Subsequently, 50 µg of RNA was treated with Lithium chloride and the clean-up protocol of the ISOLATE II RNA Mini Kit (Bioline, London, UK; Cat No BIO-52073) followed. 1 µg of cleaned RNA was used to synthesize cDNA by reverse-transcribing with oligo (dT) and random primers and Superscript II reverse transcriptase (Invitrogen). 4 µl of 16 times diluted cDNA was subjected to real-time qPCR with a Lightcycler 480 (Roche Applied Science, Basel, Switzerland), using Lightcycler SYBR Green (Roche Applied Science, Basel, Switzerland). Analysis was performed using the LinRegPCR program (AMC, Amsterdam, The Netherlands) (Ruijter et al., 2009). The target gene expression was normalized over the expression of 2 reference genes selected after analysis with the Genorm software.

Measurement of Protein Levels of Colonic Cytokines

Frozen tissue was homogenized on ice in Greenberger Lysis Buffer (150 mM NaCl, 15 mM Tris, 1 mM $MgCl_2.6H_2O$, 1 mM $CaCl_2$, 1% Triton) with complete Protease Inhibitor Cocktail (Roche Applied Science, Basel, Switzerland), pH 7.4, diluted 1:1 with PBS. Protein concentrations of interleukin (IL-)1 beta, IL-6, and tumour necrosis factor (TNF-)α were measured by sandwich enzyme-linked immunosorbent assay (ELISA; R&D systems, Abingdon, UK) according to manufacturer's protocol.

Statistical Analysis

Graphs were made using Prism 6.0 (GraphPad Software Inc., La Jolla, Calif., USA). Statistical analysis was performed using IBM SPSS Statistics Version 22.0 (IBM Corporation, New York, N.Y., USA). Statistical significance between groups was evaluated using a Mann-Whitney U test or Kruskal-Wallis Test with post-hoc Bonferroni analysis. $P<0.05$ was considered significant. *Effects of denervation in colitis model*

Figure 3:
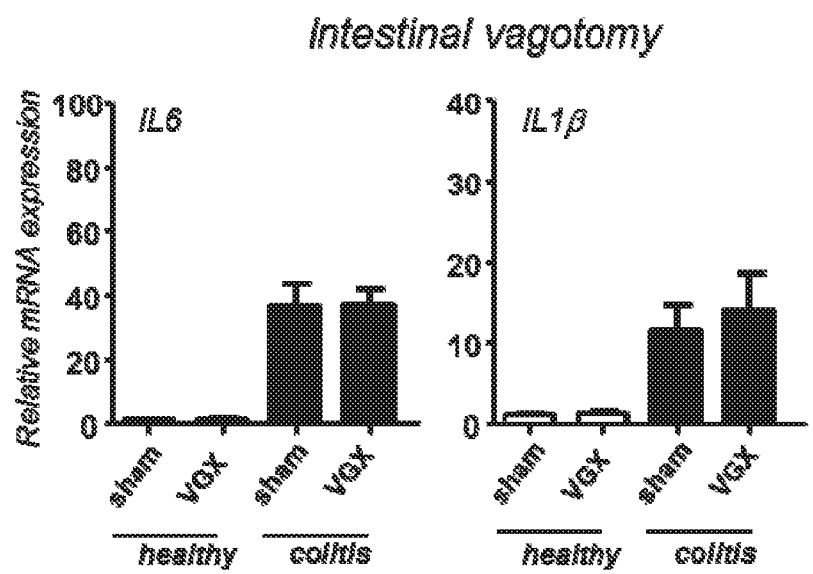
FIG. 3: Preliminary data. The effects of selective sympathectomy and vagotomy in DSS induced colitis in mice. Sympathectomy aggravates the disease course while vagotomy is without effect. Data shown are Interleukin 6 and Interleukin 1beta tissue levels, measured by ELISA at 7 days after DSS induction. Data n=8 SEM for each group. *p<0.05 ANOVA.
Figure 3:
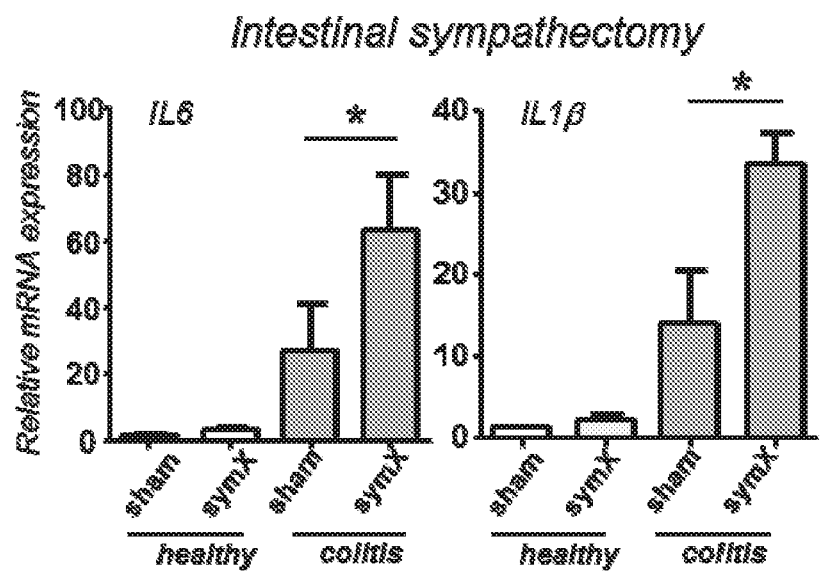

FIG. 3 shows the effects of vagotomy and sympathectomy in the mouse DSS colitis model. FIG. 3A shows that vagotomy has no effect on the levels of pro-inflammatory cytokines found in the gut tissue of colitic mice. In contrast, FIG. 3B shows that sympathectomy results in significantly higher levels of pro-inflammatory cytokines in the gut of colitis mice compared to those colitis mice with intact sympathetic gut innervation.

Figure 4:
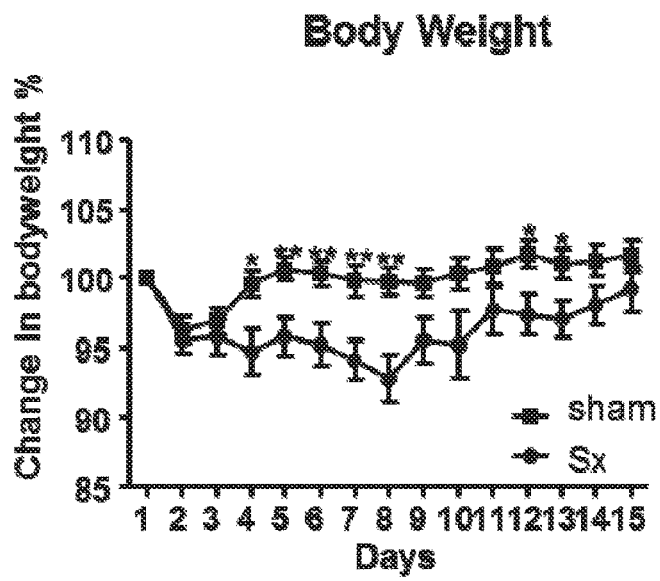
FIG. 4: Rag1−/− mice after transection of the supra mesenteric nerve (Sx) and a follow up of 16 days. A) Body weights were measured as indication of disease, shown as percentage of weight compared to the weight on day 1.
Figure 4:
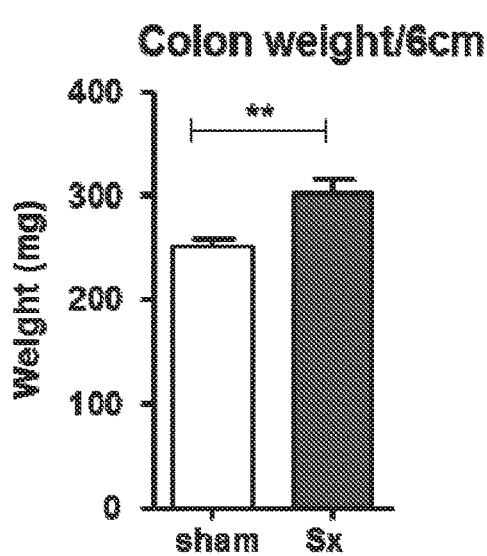
Figure 4:
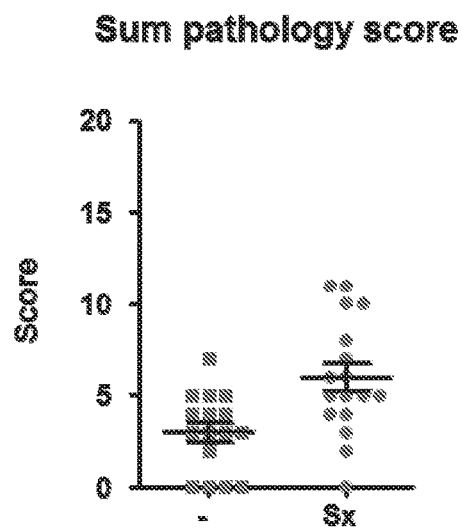
Figure 4:
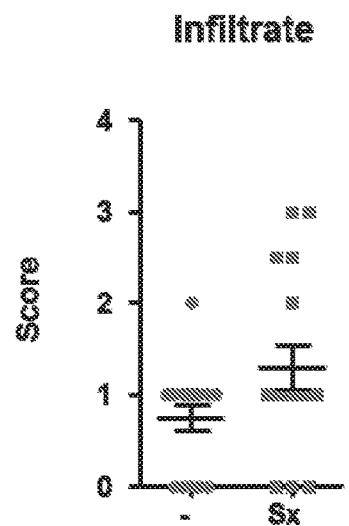
Figure 4:
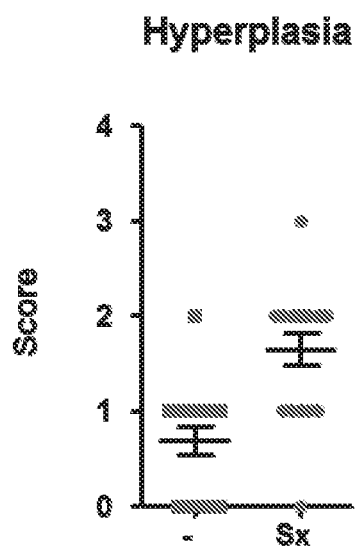
Figure 4:
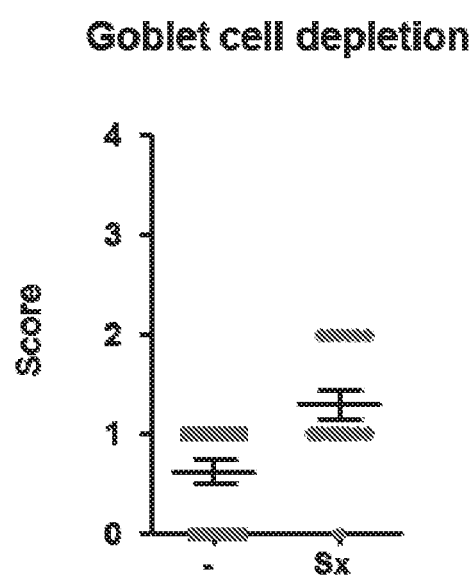
Figure 4:
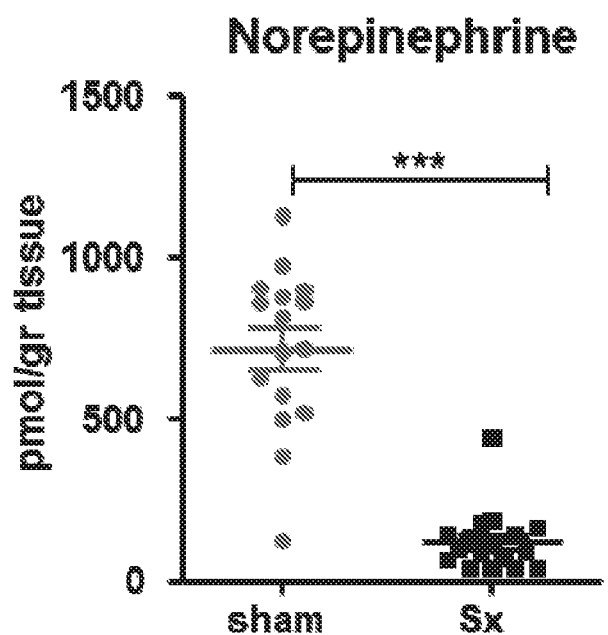

Similarly, FIG. 4 shows that the physiological and histological signs of colitis are significantly worse in DSS mice that have undergone sympathectomy. Sympathectomy mice show greater loss of body weight, increased colon weight (a sign of pathology), hyperplasia, goblet cell depletion and a greater sum pathology score compared to normal DSS mice.

These data all show that sympathectomy leads to more severe colitis symptoms in the DSS model. This worsening of symptoms correlates with the reduction in norepinephrine (NE) levels in the gut as a result of the sympathectomy (FIG. 4G).

The importance of NE in reducing inflammation is further shown in another model of colitis. When RAG mice (which exhibit higher levels of tissue NE compared to non-RAG mice) underwent sympathectomy, the mice spontaneously developed colitis and also exhibited significantly increased pro-inflammatory cytokine levels in the gut (FIG. 5). Without wishing to be bound by theory, the inventors hypothesise that the spontaneous development of colitis in RAG mice following sympathectomy is due to the higher than normal levels of NE in RAG mice and, therefore, sympathectomy has a higher impact on mucosal homeostasis and ambient NE levels, leading to spontaneous colitis.

As well as direct sympathetic innervation of the gut, the present inventors have also shown herein that sympathetic innervation of the spleen is required for an anti-inflammatory effect in the gut.

FIG. 6 shows that splenic nerve denervation results in significant increases in pro-inflammatory cytokines in the gut tissue of DSS mice. FIG. 6B also shows that splenic nerve denervation results in an increase in the total colitis pathology, as measured according to the disease activity index.

These data clearly show the importance of NE release in controlling inflammation in the gut, in particular inflammation in the colon. Moreover, these data show that the anti-inflammatory effect of NE release in the gut is not directly linked and at least partly independent from vagus nerve signalling, as vagotomy has no effect on levels of NE or on gut inflammation. Instead, the anti-inflammatory effects in the gut due to NE release is directly associated with sympathetic signalling either from distal gut-innervating sympathetic nerves (the SMP), or indirect anti-inflammatory effects of NE release triggered by sympathetic signalling from the splenic nerve.

Gut inflammation, in particular IBD and colitis, will therefore be effectively treated by inducing NE release by stimulating the SMP and/or the splenic nerve. To this end, neuromodulation devices were implanted in rat models.

Example 2

Determination of Effective Signal Parameters

In acute anaesthetised preparations rats and mice were subjected to square wave pulse electrical stimulation of the splenic nerve, superior mesenteric plexus or vagus nerves, using bipolar hook electrodes. Stimulation frequencies were kept consistent at 10 Hz, biphasic pulses with a pulse width of 50 µs. Current was varied between 1 mA and 10 mA. The duration of stimulation was either 2 or 10 minutes. 1 mA for 2 minutes was observed to be the most effective at inducing NE release (See FIG. 7 and below).

A cuff electrode was also developed for the superior mesenteric nerve that allowed encapsulation of the superior mesenteric plexus together with the mesenteric artery. The diameter of the cuff was determined to be optimal at 500 um and 5 mm in length to interface with that anatomy. A tripolar configuration of electrodes allows for current to be delivered within the centre of the cuff without significant current leakage out to surrounding tissue.

Further optimisation of signal parameters was performed for the cuff electrode in a two-step process. Initial optimisation was performed using the sciatic nerve. The sciatic nerve was exposed and 1 mA and 10 Hz stimulation was applied to the nerve using the cuff. This elicited obvious muscle contractions. Stimulation was reduced until only slight muscle movement was induced—this was determined to be the activation threshold (160-185 uA minimum to induce a response).

In order to optimise the signal for application to the superior mesenteric plexus, signals of 200 µA, 400 µA and 600 µA were applied to the plexus. Telemetric EMG recordings (FIG. 8) and levels of arterial and venous perfusion of the mesentery (FIG. 9) were measured in order to optimise the signal with respect to minimum side-effects.

Figure 8A:
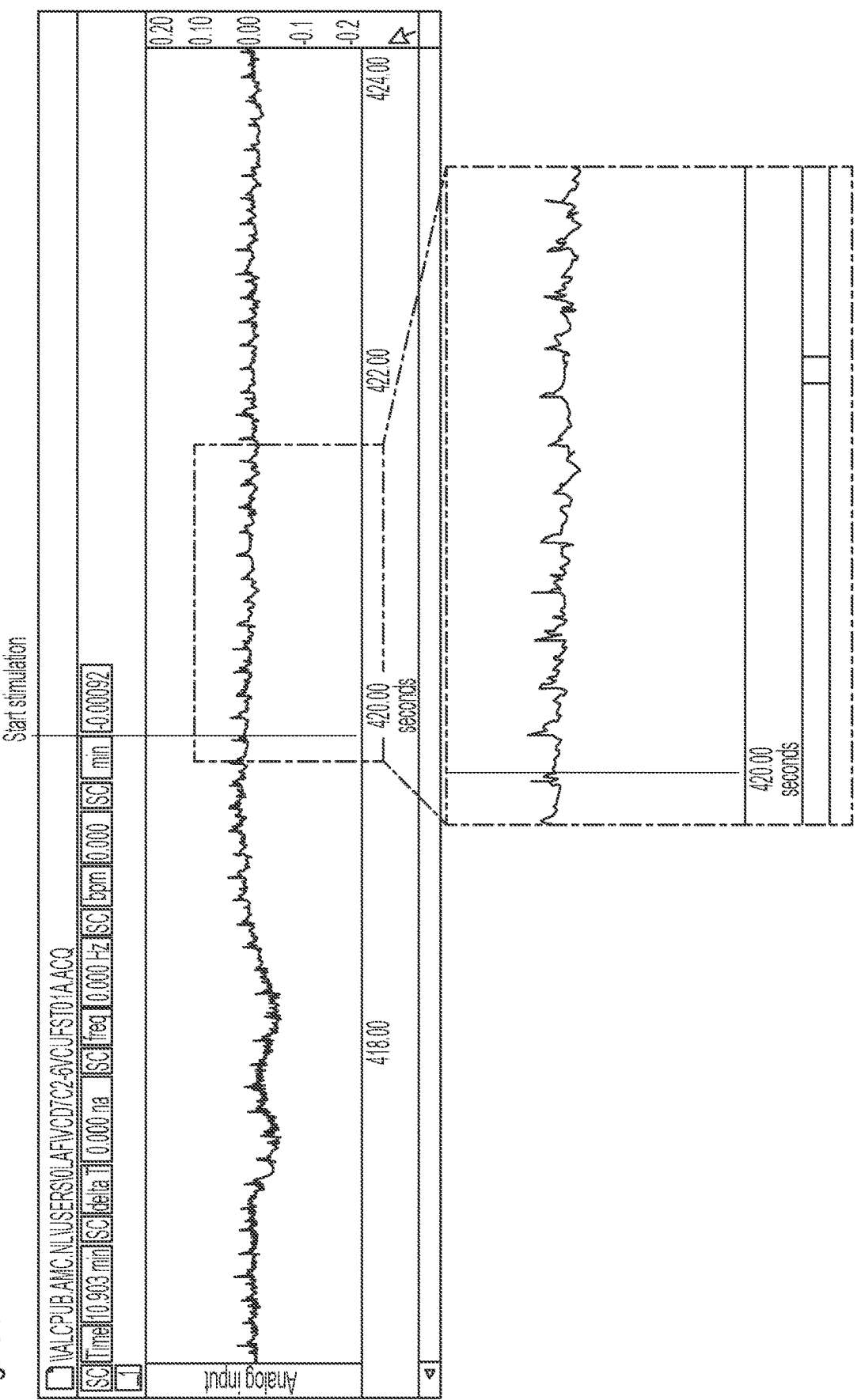
Figure 8B:
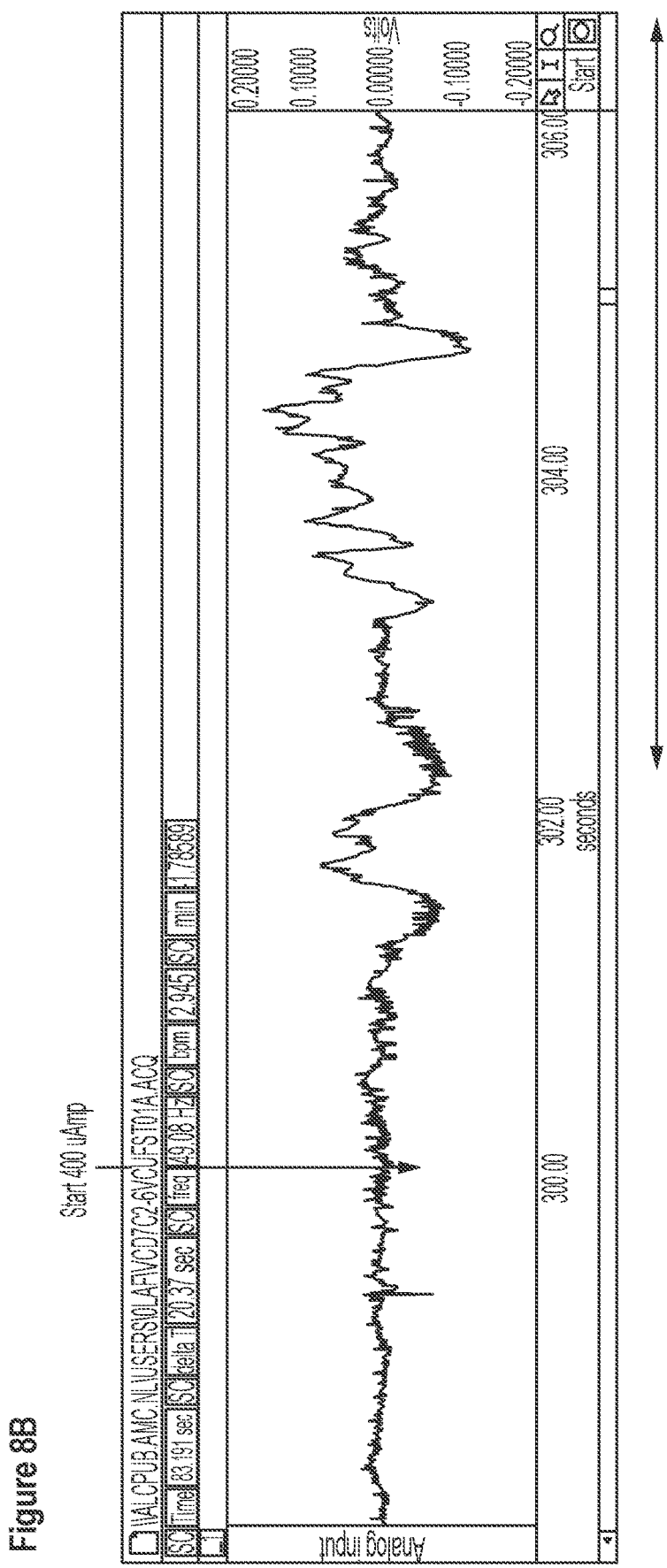

FIG. 8A shows that minimal, if any, EMG response is observed with a 200 µA signal, with no clear change in tracing following the start of stimulation. This indicates that there is little or no signal leakage to other nerves that has triggered discomfort or other side-effects. FIG. 8B shows that application of a signal of 400 µA induced a change in EMG activity. Based on behavioural changes in the rat, such a change was not attributed to pain. Nonetheless, the signal was clearly noticeable by the animal.

FIG. 9 shows changes in venous (A) and arterial (B) perfusion of the mesentery following application of signals of 200 µA, 400 µA, and 600 µA. Signals of 200 µA and 400 µA had minimal effect on venous or arterial flow, but a signal of 600 µA resulted in abnormal venous and arterial flow, an indication of unwanted side-effects of the signal.

This method can be used to identify the optimal signal to be applied to the superior mesenteric plexus in order to effectively stimulate whilst minimising unwanted side-effects. In this case, the optimal signal parameters for stimulating the rat SMP is 10 Hz, 2 mins duty, 160-200 µA biphasic pulses, pulse width of 50 µs. An analogous method may be used to optimise the signal for neuromodulation of the splenic nerve and for determining appropriate signal parameters in human patients.

Stimulation of NE Release

FIG. 7 provides data showing NE release from the stimulated nerve (either splenic nerve (shown as "splen") or SMP (shown as "mes")). Stimulation of both the splenic nerve and SMP resulted in increased NE release in the spleen and distal colon. Optimal NE release occurred at 1 mA and 2 mins duration (much lower than conventional vagus nerve stimulation paradigms). Higher stimulation parameters yielded no further improvements in response.

Stimulation of the splenic nerve SMP produced a more robust NE response than vagal stimulation and with few side effects. Indeed no NE was released in the spleen following vagus nerve stimulation, indicating any anti-inflammatory effect as a result of vagal stimulation is due to a different mechanism than that demonstrated herein. As a result, modulation of splenic nerve and/or SMP neural activity is not only expected to have fewer unwanted systemic effects compared to vagal signalling, but allows access to a new therapeutic anti-inflammatory mechanism.

Figure 1:
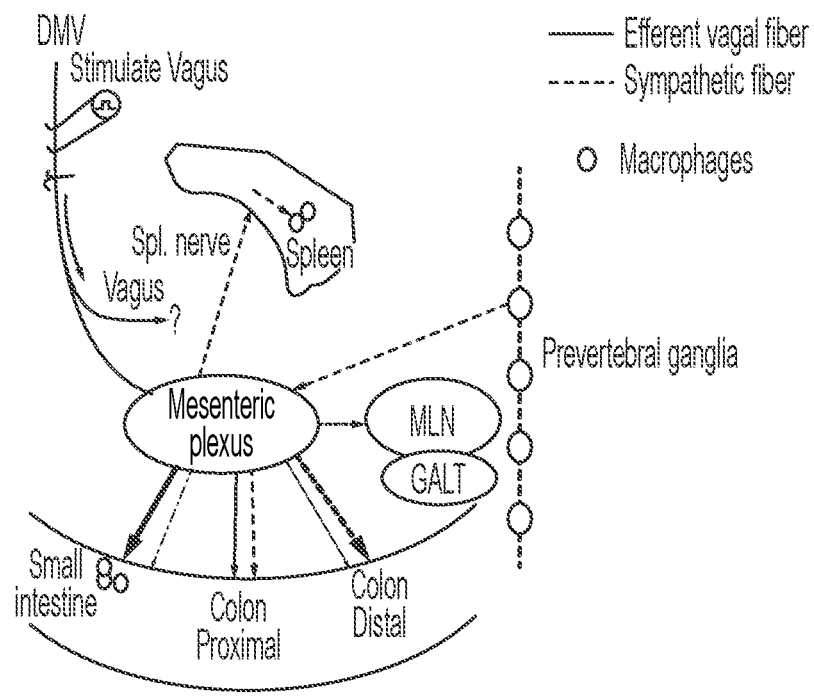
FIG. 1: A. A schematic illustration of the interactive parasympathetic and sympathetic innervation of lymphoid structures. Efferent vagal innervation (solid), originating in the dorsal motor nucleus of the vagus nerve (DMV) innervates the gut mesenteric plexus and muscularis externa where resident macrophage-like cells are in anatomical association to vagus nerve endings. The proximal intestine is more densely innervated by extrinsic vagus innervation compared to distal segments. Sympathetic innervation (dashed) arising from the prevertebral ganglia follow a gradient opposite to the vagal innervation, this is reflected by thickness of the arrows. Sympathetic innervation exists for lymphoid organs (e.g., GALT and mesenteric lymph nodes (MLNs)). B. A schematic illustration of neuronal pathways of intervention. Indicated are the most relevant sympathetic routes of stimulation/denervation. The splenic nerve is aligned with the splenic artery and constitutes a inter-arterial plexus (lienal plexus). This plexus follows the artery to the spleen, branching off, subsidiary plexuses along the pancreatic and gastric branches of the artery. Shown in dotted lines are pathways of intervention in DSS colitis experiments as described in this application.
Figure 1:
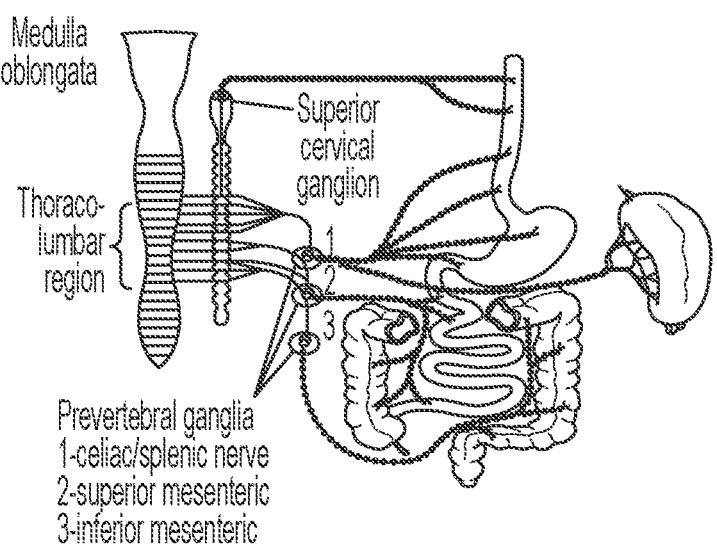

It has been shown that activation of adrenergic receptors (ARs) results in a reduction in pro-inflammatory cytokine production by dendritic cells (DCs), whether that activation is by adrenergic neurotransmitters (epinephrine) or an artificial AR agonist (salbutamol) (FIG. 1 of Nijhuis. L et al, PLoS One. 2014; 9(1), incorporated herein by reference). Therefore, the increase in tissue NE induced by the neuromodulation of the SMP or splenic nerve is expected to have the same anti-inflammatory effect.

Moreover, superior mesenteric plexus and splenic nerve stimulation each produced significant NE responses in the spleen and the lower intestinal tract and colon, but with less NE release observed in the upper intestinal system. Stimulation of these nerves will therefore be particularly effective in treating forms of gut inflammation such as IBD, which are frequently (Crohn's disease) or exclusively located in the lower intestine and colon. These areas of the gut have little if any vagal innervation and, therefore, respond poorly to vagal stimulation. By stimulating the SMP or splenic nerve, it is newly possible to target inflammation in these areas of the gut.

Example 3

Neuromodulation Via the Superior Mesenteric Plexus

Stimulation of the SMP was achieved used implanted cuff electrodes attached to the Mesenteric Nerve. Implantation was performed surgically prior to experimentation.

FIG. 10 shows the timeline of surgical implantation, gift of DSS to induce colitis, stimulation paradigm for electrical stimulation of the SMP, and day of sacrifice and analyses of biomarkers of disease.

Figure 11:
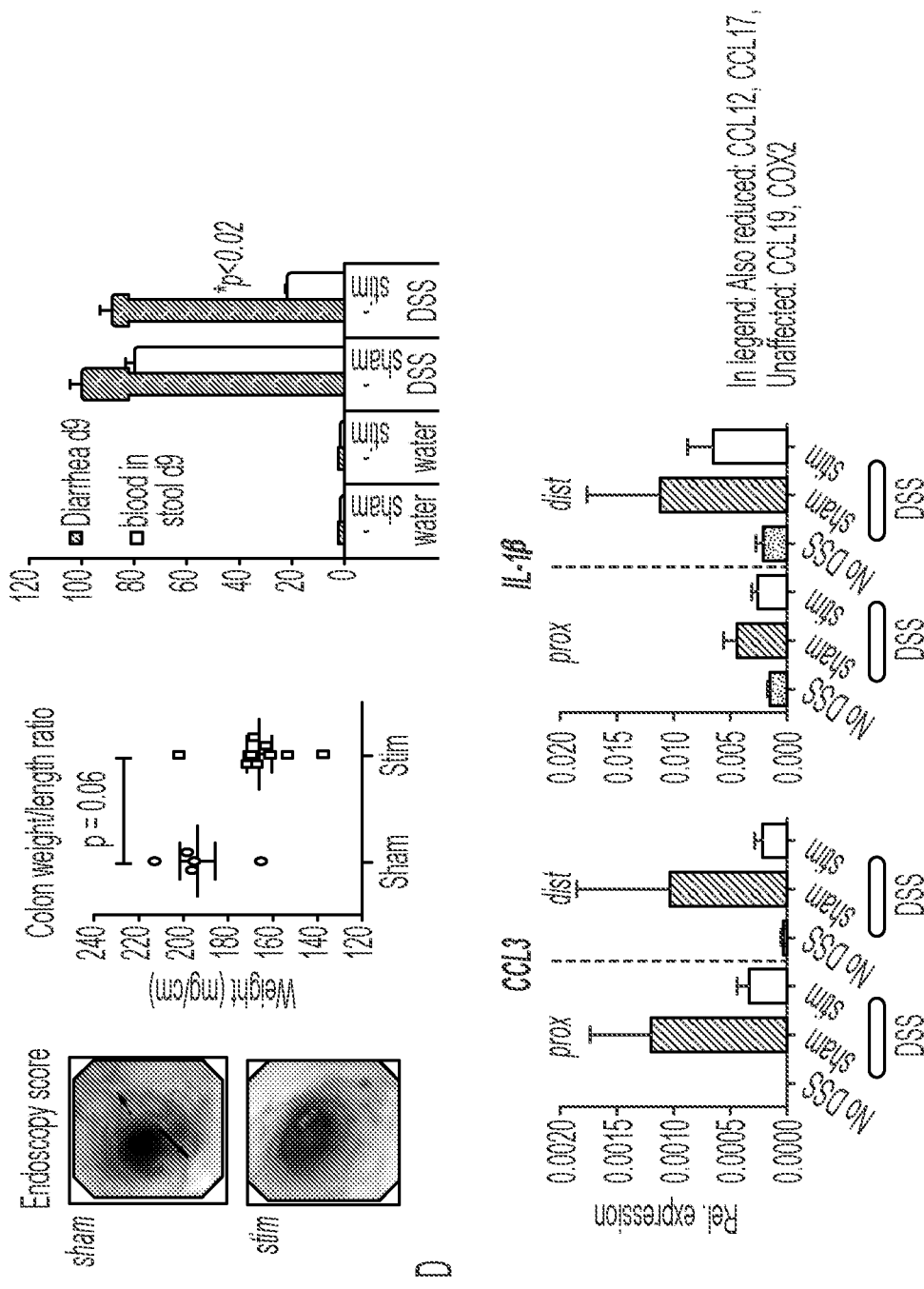

FIG. 11 shows the experimental outcomes of the SMP stimulation intervention in DSS colitis in rat, as in FIG. 10. Shown are the visualisation of the improved endoscopy appearance of colon at day 9 of DSS colitis under sham and stimulated condition. Further, FIG. 11B shows clinical parameters of improved colon weight/length ratio measured in rat colons at day 9 of DSS colitis. Further, improved clinical parameters of colitis at day 9 of DSS were seen in rats undergoing stimulation of SMP, as parameters such as diarrhea and blood in stool. The stimulation treatment down regulated transcription of cytokines and chemokines in colitis colon homogenates as determined by QPCR. Importantly, selected biomarkers for QPCR were deduced from QPCR array screening (SA Biosciences human inflammation kit) that showed up-regulation of CCL3, CCL12, CCL17, IL1b in rat DSS at day 9. Up-regulation of colonic levels of CCL3, IL1b, CCL12, and CCL17 were equally reduced; whilst CCL19 and COX 2 were unaffected by stimulation.

FIG. 12 shows the histology scores in rat colon as assessed by a blinded experienced pathologist (Dr S Meijer, AMC, Pathology). Colon histology markers for inflammation were significantly reduced by SMN stimulation, as depicted in FIG. 10.

Example 4

Sympathetic Denervation of the Spleen

FIG. 13 shows the results of spleen denervation for colitis disease course. Here the effect of splenic nerve denervation on the course of colitis is visualized. Splenic denervation surgery was performed prior to DSS colitis, and expression of colon homogenate transcripts was performed. The following transcripts were measured: Extracellular Matrix & Cell Adhesion: COL14A1, COL1A1, COL1A2, COL3A1, COL4A1, COL4A3, COL5A1, COL5A2, COL5A3, VTN; Remodeling Enzymes: Ctsg, Ctsk, Ctsl, F13a1, F3 (Tissue Factor), Fga (Fibrinogen), Mmp1a, Mmp2, Mmp7, Mmp9, Plat (tPA), Plau (uPA), Plaur (uPAR), Pig, Serpine1 (PAI-1), Timp1; Cellular Adhesion: Cdh1 (E-cadherin), Itga1, Itga2, Itga3, Itga4, Itga5, Itga6, Itgav, Itgb1, Itgb3, Itgb5, Itgb6; Cytoskeleton: Acta2 (a-SMA), Actc1, Rac1, Rhoa, Tagln; Inflammatory Cytokines & Chernokines: Ccl12, Ccl7 (Mcp-3), Cd40lg (Tnfsf5), Cxcl1, Cxcl11 (I-TAC/IP-9), Cxcl3, Cxcl5 (ENA-78/LIX), Ifng, Il10, Il1B, Il2, Il4, Il6; Growth Factors: Angpt1, Csf2 (GM-CSF), Csf3 (GCSF), Ctgf, Egf, Fgf10, Fgf2, Fgf7, Hbegf (Dtr), Hgf, Igf1, Mif, Pdgfa, Tgfa, Tgfb1, Tnf, Vegfa; Signal Transduction: TGFβ: Tgfb1, Tgfbr3, Stat3, WNT: Ctnnb1, Wisp1, Wnt5a; Phosphorylation: Mapk1 (Erk2), Mapk3 (Erk1), Pten, Receptors: Egfr, Il6st (Gp130); Other: PTGS2. Elevated expression profiles for inflammatory genes are seen after splx (splenic nerve lesion) as compared to sham surgery. In addition, splenic nerve lesion leads to enhance in the Disease Activity Index (panel C) induced by DSS administration. Further, spleen denervation leads to a significant increase in the expression level of the pro-inflammatory cytokines IL-6 and TNFα as well as of IL-1β.

The invention claimed is:

1. An apparatus or system for modulating the neural activity of the superior mesenteric plexus (SMP) of a patient, the apparatus or system comprising:
a first transducer comprising a cuff electrode configured to encompass the SMP and the superior mesenteric artery, the first transducer configured to apply a first electrical stimulatory signal to the SMP; and
a controller coupled to the first transducer, the controller controlling the first electrical stimulatory signal to be applied by the first transducer, such that the first electrical stimulatory signal increases the neural activity of a nerve to which it is applied to produce an increase in local sympathetic tone in the spleen and/or gut of the subject.

2. An apparatus or system for treating an inflammatory disorder in a patient, the apparatus or system comprising:
a first transducer comprising a cuff electrode configured to encompass the SMP and the superior mesenteric artery, the first transducer configured to apply a first electrical stimulatory signal to the superior mesenteric plexus (SMP) of the patient; and
a controller coupled to the first transducer, the controller controlling the first electrical stimulatory signal to be applied by the first transducer, such that the first electrical stimulatory signal increases the neural activity of a nerve to which it is applied to produce an increase in local sympathetic tone in the spleen and/or gut of the patient.

3. An apparatus or system according to claim 1, wherein the increase in local sympathetic tone comprises an increase in gut (intestine and/or colon) tissue and/or circulating nor-epinephrine.

4. An apparatus or system according to claim 1, wherein the controller is coupled to a detector element to detect one or more physiological parameters in the patient, and the controller causes the first transducer to apply the first electrical stimulatory signal when the physiological parameter is detected to be meeting or exceeding a predefined threshold value, wherein one or more of the detected physiological parameters is selected from: sympathetic tone; gut tissue and/or circulating nor-epinephrine (NE) levels; gut tissue and/or circulating substance P levels; gut tissue and/or circulating levels of one or more inflammatory markers.

5. An apparatus or system according to claim 1, wherein the apparatus or system is suitable for at least partial implantation into the patient, optionally full implantation into the patient.

6. A method of treating colitis in a patient comprising:
i. implanting in the patient an apparatus or system according to claim 1;
ii. positioning the cuff electrode around and in signalling contact with the SMP and the superior mesenteric artery of the patient;
iii. activating the apparatus or system to apply the first electrical stimulatory signal to the SMP;
thereby modulating neural activity of the splenic nerve and/or SMP of the patient.

7. A method according to claim 6, further comprising:
positioning a second transducer in signalling contact with the splenic nerve of the patient; and
activating the apparatus or system to apply a second stimulatory signal to the splenic nerve, thereby modulating neural activity of the splenic nerve.

8. A method according to claim 6, wherein at least one device or apparatus comprising the first transducer is at least partially implanted in the patient, optionally wholly implanted in the patient.

9. A method according to claim 6, wherein treatment of the colitis is indicated by an increase in local sympathetic tone in the spleen and/or gut.

10. A method according to claim 6, wherein the increase in local sympathetic tone comprises an increase in gut tissue and/or circulating nor-epinephrine.

11. A method according to claim 6, wherein the first stimulatory signal is applied intermittently.

12. A method according to claim 6, further comprising the step of detecting one or more physiological parameters in the patient, wherein the first electrical stimulatory signal is applied only when the detected physiological parameter meets or exceeds a predefined threshold value, wherein one or more detected physiological parameters is selected from: sympathetic tone; gut tissue and/or circulating nor-epinephrine (NE) levels; gut tissue and/or circulating substance P levels; gut tissue and/or circulating levels of one or more inflammatory markers.

13. An apparatus or system of claim 1, wherein the first electrical stimulatory signal comprises an alternative current (AC) waveform.

14. An apparatus or system of claim 1, further comprising:
a second transducer configured to apply a second stimulatory signal to the splenic nerve, wherein the controller is further coupled to the second transducer, the controller controlling the second stimulatory signal to be applied by the second transducer, such that the second stimulatory signal increases the neural activity of a nerve to which it is applied to produce an increase in local sympathetic tone in the spleen.

15. An apparatus or system of claim 14, wherein the first electrical stimulatory signal and the second stimulatory signal applied by the first transducer and the second transducer, respectively, are independently selected.

* * * * *